United States Patent
Chang et al.

(10) Patent No.: US 10,201,423 B2
(45) Date of Patent: Feb. 12, 2019

(54) DEVICES, SYSTEMS, AND METHODS FOR RESHAPING A HEART VALVE ANNULUS

(71) Applicant: MVRx, INC., Moss Beach, CA (US)

(72) Inventors: Robert T. Chang, Belmont, CA (US); Timothy R. Machold, Moss Beach, CA (US); David A. Rahdert, San Francisco, CA (US); Jason Rogers, Sacramento, CA (US)

(73) Assignee: MVRx, Inc., San Mateo, CA (US)

( * ) Notice: Subject to any disclaimer, the term of this patent is extended or adjusted under 35 U.S.C. 154(b) by 206 days.

(21) Appl. No.: 14/918,205

(22) Filed: Oct. 20, 2015

(65) Prior Publication Data
US 2016/0262887 A1 Sep. 15, 2016

Related U.S. Application Data

(60) Provisional application No. 62/131,688, filed on Mar. 11, 2015.

(51) Int. Cl.
*A61F 2/24* (2006.01)
*A61B 17/04* (2006.01)
(Continued)

(52) U.S. Cl.
CPC ........ *A61F 2/2442* (2013.01); *A61B 17/0401* (2013.01); *A61F 2/06* (2013.01);
(Continued)

(58) Field of Classification Search
CPC ........ A61F 2/06; A61F 2/2442; A61F 2/2445; A61F 2/2466; A61F 2/2478;
(Continued)

(56) References Cited

U.S. PATENT DOCUMENTS

| 4,056,854 A | 11/1977 | Boretos et al. |
| 4,275,469 A | 6/1981 | Gabbay |

(Continued)

FOREIGN PATENT DOCUMENTS

| WO | 03055417 | 7/2003 |
| WO | 2004045463 | 6/2004 |
| WO | 2016144391 | 9/2016 |

OTHER PUBLICATIONS

Alpert et al., Tricuspid valve disease, Valvular Heart Disease, Philadelphia, PA: Lippincott Williams and Wilkins, 2000, pp. 377-392.

(Continued)

*Primary Examiner* — Wade Miles
*Assistant Examiner* — George J Ulsh
(74) *Attorney, Agent, or Firm* — Kilpatrick Townsend & Stockton LLP

(57) ABSTRACT

Implants or systems of implants and methods apply a selected force vector or a selected combination of force vectors within or across the right atrium, which allow tricuspid valve leaflets to better coapt. The implants or systems of implants and methods make possible rapid deployment, facile endovascular delivery, and full intra-atrial retrievability. The implants or systems of implants and methods also make use of strong fluoroscopic landmarks. The implants or systems of implants and methods make use of an adjustable implant. The implants or systems of implants and methods may utilize a bridge stop to secure the implant.

21 Claims, 13 Drawing Sheets

(51) Int. Cl.
*A61F 2/06* (2013.01)
*A61B 17/00* (2006.01)

(52) U.S. Cl.
CPC .......... *A61F 2/2445* (2013.01); *A61F 2/2466* (2013.01); *A61F 2/2478* (2013.01); *A61B 2017/00243* (2013.01); *A61B 2017/00575* (2013.01); *A61B 2017/00592* (2013.01); *A61B 2017/00606* (2013.01); *A61B 2017/048* (2013.01); *A61B 2017/0414* (2013.01); *A61B 2017/0419* (2013.01); *A61B 2017/0441* (2013.01); *A61B 2017/0464* (2013.01); *A61F 2/2403* (2013.01); *A61F 2/2487* (2013.01); *A61F 2250/006* (2013.01)

(58) Field of Classification Search
CPC .................. A61F 2/2403; A61F 2/2487; A61F 2250/006; A61F 2/02; A61F 2/24; A61B 17/0057; A61B 17/0401; A61M 25/01
See application file for complete search history.

(56) References Cited

U.S. PATENT DOCUMENTS

| | | |
|---|---|---|
| 4,994,069 A | 2/1991 | Ritchart et al. |
| 5,269,759 A | 12/1993 | Hernandez et al. |
| 5,360,444 A | 11/1994 | Kusuhara |
| 5,370,685 A | 12/1994 | Stevens |
| 5,492,538 A | 2/1996 | Johlin, Jr. |
| 5,507,731 A | 4/1996 | Hernandez et al. |
| 5,545,241 A | 8/1996 | Vanderauwera et al. |
| 5,624,430 A | 4/1997 | Eton et al. |
| 5,716,397 A | 2/1998 | Myers |
| 5,776,189 A | 7/1998 | Khalid |
| 5,792,155 A | 8/1998 | Van Cleef |
| 5,830,224 A | 11/1998 | Cohn et al. |
| 5,851,185 A | 12/1998 | Berns |
| 5,855,601 A | 1/1999 | Bessler et al. |
| 5,895,404 A | 4/1999 | Ruiz |
| 5,916,194 A | 6/1999 | Jacobsen et al. |
| 5,961,440 A | 10/1999 | Schweich, Jr. et al. |
| 6,026,814 A | 2/2000 | Lafontaine et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,077,214 A | 6/2000 | Mortier et al. |
| 6,099,542 A | 8/2000 | Cohn et al. |
| 6,102,932 A | 8/2000 | Kurz |
| 6,162,168 A | 12/2000 | Schweich, Jr. et al. |
| 6,165,119 A | 12/2000 | Schweich, Jr. et al. |
| 6,183,411 B1 | 2/2001 | Mortier et al. |
| 6,210,432 B1 | 4/2001 | Solem et al. |
| 6,231,587 B1 | 5/2001 | Makower |
| 6,260,552 B1 | 7/2001 | Mortier et al. |
| 6,261,222 B1 | 7/2001 | Schweich, Jr. et al. |
| 6,287,339 B1 | 9/2001 | Vazquez et al. |
| 6,299,637 B1 | 10/2001 | Shaolian et al. |
| 6,312,464 B1 | 11/2001 | Navia |
| 6,312,465 B1 | 11/2001 | Griffin et al. |
| 6,332,864 B1 | 12/2001 | Schweich, Jr. et al. |
| 6,332,893 B1 | 12/2001 | Mortier et al. |
| 6,338,470 B1 | 1/2002 | Steely et al. |
| 6,338,735 B1 | 1/2002 | Stevens |
| 6,338,740 B1 | 1/2002 | Carpentier |
| 6,352,543 B1 | 3/2002 | Cole |
| 6,385,472 B1 | 5/2002 | Hall et al. |
| 6,402,781 B1 | 6/2002 | Langberg et al. |
| 6,419,695 B1 | 7/2002 | Gabbay |
| 6,419,696 B1 | 7/2002 | Ortiz et al. |
| 6,440,164 B1 | 8/2002 | Dimatteo et al. |
| 6,454,799 B1 | 9/2002 | Schreck |
| 6,458,153 B1 | 10/2002 | Bailey et al. |
| 6,503,272 B2 | 1/2003 | Duerig et al. |
| 6,514,194 B2 | 2/2003 | Schweich, Jr. et al. |
| 6,537,198 B1 | 3/2003 | Vidlund et al. |
| 6,589,160 B2 | 7/2003 | Schweich, Jr. et al. |
| 6,616,684 B1 | 9/2003 | Vidlund et al. |
| 6,626,899 B2 | 9/2003 | Houser et al. |
| 6,629,534 B1 | 10/2003 | Goar St. et al. |
| 6,652,540 B1 | 11/2003 | Cole et al. |
| 6,656,221 B2 | 12/2003 | Taylor et al. |
| 6,669,679 B1 | 12/2003 | Savage et al. |
| 6,669,709 B1 | 12/2003 | Cohn et al. |
| 6,676,699 B2 | 1/2004 | Shiu |
| 6,685,739 B2 | 2/2004 | Dimatteo et al. |
| 6,702,826 B2 | 3/2004 | Liddicoat et al. |
| 6,709,456 B2 | 3/2004 | Langberg et al. |
| 6,723,038 B1 | 4/2004 | Schroeder et al. |
| 6,764,510 B2 | 7/2004 | Vidlund et al. |
| 6,793,618 B2 | 9/2004 | Schweich, Jr. et al. |
| 6,805,711 B2 | 10/2004 | Quijano et al. |
| 6,893,459 B1 | 5/2005 | Macoviak |
| 6,913,608 B2 | 7/2005 | Liddicoat et al. |
| 6,945,978 B1 | 9/2005 | Hyde |
| 7,004,176 B2 | 2/2006 | Lau |
| 7,070,618 B2 | 7/2006 | Streeter |
| 7,077,862 B2 | 7/2006 | Vidlund et al. |
| 7,166,126 B2 | 1/2007 | Spence et al. |
| 7,967,808 B2 | 6/2011 | Fitzgerald et al. |
| 8,597,348 B2 | 12/2013 | Meiri et al. |
| 9,504,570 B2 | 11/2016 | Bobo, Jr. et al. |
| 9,522,006 B2 | 12/2016 | Cohn et al. |
| 9,572,667 B2 | 2/2017 | Solem et al. |
| 9,636,223 B2 | 5/2017 | Spinner et al. |
| 2001/0010017 A1 | 7/2001 | Letac et al. |
| 2001/0021872 A1 | 9/2001 | Bailey et al. |
| 2001/0051824 A1 | 12/2001 | Hopkins et al. |
| 2002/0010481 A1 | 1/2002 | Jayaraman |
| 2002/0032481 A1 | 3/2002 | Gabbay |
| 2002/0094573 A1 | 7/2002 | Bell |
| 2002/0123802 A1 | 9/2002 | Snyders |
| 2002/0129820 A1 | 9/2002 | Ryan et al. |
| 2002/0138138 A1 | 9/2002 | Yang |
| 2002/0183841 A1 | 12/2002 | Cohn et al. |
| 2003/0014104 A1 | 1/2003 | Cribier |
| 2003/0040792 A1 | 2/2003 | Gabbay |
| 2003/0069593 A1 | 4/2003 | Tremulis et al. |
| 2003/0078465 A1 | 4/2003 | Pai et al. |
| 2003/0120340 A1 | 6/2003 | Liska et al. |
| 2003/0139819 A1 | 7/2003 | Beer et al. |
| 2003/0169347 A1 | 9/2003 | Jenkins et al. |
| 2003/0181928 A1 | 9/2003 | Vidlund et al. |
| 2003/0199974 A1 | 10/2003 | Lee et al. |
| 2003/0233022 A1 | 12/2003 | Vidlund et al. |
| 2004/0148019 A1 | 7/2004 | Vidlund et al. |
| 2004/0162610 A1 | 8/2004 | Liska et al. |
| 2004/0243230 A1 | 12/2004 | Navia et al. |
| 2004/0260317 A1 | 12/2004 | Bloom et al. |
| 2005/0010277 A1 | 1/2005 | Chuter |
| 2005/0075723 A1 | 4/2005 | Schroeder et al. |
| 2005/0267571 A1 | 12/2005 | Spence et al. |
| 2006/0241745 A1 | 10/2006 | Solem |
| 2006/0282161 A1 | 12/2006 | Huynh et al. |
| 2007/0282430 A1 | 12/2007 | Thommen et al. |
| 2011/0106244 A1 | 5/2011 | Ferrari et al. |
| 2011/0184510 A1 | 7/2011 | Maisano et al. |
| 2012/0035718 A1 | 2/2012 | Chang et al. |
| 2016/0242762 A1 | 8/2016 | Lynn et al. |
| 2016/0270916 A1 | 9/2016 | Robinson et al. |
| 2016/0354076 A1 | 12/2016 | Groothuis et al. |
| 2017/0086975 A1 | 3/2017 | Gilmore et al. |
| 2017/0189171 A1 | 7/2017 | Sutherland et al. |

OTHER PUBLICATIONS

Alvarez et al., Technical Improvements in the Repair of Acute Postinfarction Ventricular Septal Rupture, J Card Surg., vol. 7, No. 3, Sep. 1992, pp. 198-202.

Antunes, Submitralleft Ventricular Aneurysms. Correction by a New Transatrial Approach, J Thorac Cardiovasc Surg., vol. 94, No. 2, Aug. 1987, pp. 241-245.

(56) References Cited

OTHER PUBLICATIONS

Aoyagi et al., Modified De Vega's annuloplasty for functional tricuspid regurgitation-early and late results, The Kurume Medical Journal, vol. 39, No. 1, 1992, pp. 23-32.
Bailey et al., Surgical Repair of Mitral Insufficiency, Diseases of the Chest, vol. XIX, No. 2, Feb. 1951, pp. 125-137.
Bailey et al., The Surgical Correction of Mitral Insufficiency by the Use of Pericardia! Grafts, The Journal of Thoracic Surgery, vol. 28, No. 6, Dec. 1954, pp. 551-603.
Barnard et al., A Surgical Approach to Mitral Insufficiency, Br J Surg., vol. 48, May 1961, pp. 655-662.
Bolling et al., Early Outcome of Mitral Valve Reconstruction in Patients with End-Stage Cardiomyopathy, J Thorac Cardiovasc Surgical, vol. 109, 1995, pp. 676-683.
Bolling et al., Intermediate-Term Outcome of Mitral Reconstruction in Cardiomyopathy, Journal of Thoracic Cardiovascular Surgery, vol. 115, No. 2, Feb. 1998, pp. 381-388.
Bonow et al., ACC/AHA 2006 guidelines for the management of patients with valvular heart disease . . . , Circulation, vol. 114, No. 5, Aug. 1, 2006, pp. e84-e231.
Cicek et al., Left Ventricular Endoaneurysmorrhaphy: Effect on Left Ventricular Size, Shape and Function, Cardiology, vol. 88, No. 4, Jul.-Aug. 1997, pp. 340-345.
Cohn, Tricuspid regurgitation secondary to mitral valve disease: when and how to repair, Journal of cardiac surgery, vol. 9, Suppl 2, Mar. 1994, pp. 237-241.
Cooley, Repair of Postinfarction Ventricular Septal Defect, J Card Surg., vol. 9, No. 4, Jul. 1994, pp. 427-429.
Cox, Surgical Management of Left Ventricular Aneurysms: A Clarification of the Similarities and Differences Between . . . , Sernin Thorac Cardiovasc Surg., vol. 9, No. 2, Apr. 1997, pp. 131-138.
Daggett et al., Surgery for Post-Myocardial Infarct Ventricular Septal Defect, Ann Surg., vol. 186, No. 3, Sep. 1977, pp. 260-271.
Daggett, Surgical Technique for Early Repair of Posterior Ventricular Septal Rupture, J Thorac Cardiovasc Surg., vol. 84, No. 2, Aug. 1982, pp. 306-312.
Davila et al., A Method for the Surgical Correction of Mitral insufficiency, Surgery, Gynecology and Obstetrics, vol. 98, No. 4, Apr. 1954, pp. 407-412.
Davila et al., Circumferential Suture of the Mitral Ring: A Method for the Surgical Correction of Mitral Insufficiency, Journ of Thoracic Surg, vol. 30, No. 5, Nov. 1955, pp. 531-560.
Davila et al., The Clinical and Physiological Criteria for Surgical Correction of Mitral Insufficiency, Journal of Thoracic Surg, vol. 35, No. 2, Feb. 1958, pp. 206-231.
Da Silva et al., Postinfarction Ventricular Septal Defect an Efficacious Technique for Early Surgical Repair, J Thorac Cardiovasc Surg., vol. 97, No. 1, Jan. 1989, pp. 86-89.
Deloche et al., Anatomical study of rheumatic tricuspid valve diseases . . . , Annales de chirurgie thoracique et cardio-vasculaire, vol. 12, No. 4, Oct. 1973, pp. 343-349.
Dor, Left Ventricular Aneurysms: the Endoventrciular Circular Patch Plasty, Semin Thorac Cardiovasc Surg., vol. 9, No. 2, Apr. 1997, pp. 123-130.
Dreyfus et al., Secondary tricuspid regurgitation or dilatation: which should be the criteria for surgical repair?, The Annals of Thoracic Surgery, vol. 79, No. 1, Jan. 2005, pp. 127-132.
Edmunds et al., Septal Defect, Atlas of Cardiothoracic Surgery, 1990.
Fucci et al., Improved Results with Mitral Valve Repair Using New Surgical Techniques, European Journal of Cardio-Throacic Surgery, vol. 9, 1995, pp. 621-626.
Fukuda et al., Three-dimensional geometry of the tricuspid annulus . . . , Circulation, vol. 114, Suppl. 1, Jul. 4, 2006, pp. I492-I498.
Fukuda et al., Tricuspid valve tethering predicts residual tricuspid regurgitation after tricuspid annuloplasty, Circulation, vol. 111, No. 8, Mar. 1, 2005, pp. 975-979.

Glover et al., The Treatment of Mitral Insufficiency by the Purse-String Technique, Journal of Thoracic Surgery, vol. 33, No. 1, Jan. 1957, pp. 75-101.
Harken et al., The Surgical Correction of Mitral Insufficiency, Surgical Forum, vol. 4, 1953, pp. 4-7.
Harken et al., The Surgical Correction of Mitral Insufficiency, The Journal of Thoracic Surgery, vol. 28, No. 6, 1954, pp. 604-624.
Harlan et al., Manual of Cardiac Surgery, vol. 2, Figs. 16.3-16.4, 1981.
Henderson et al., The Surgical Treatment of Mitral Insufficiency, Annals of Surgery. vol. 142, No. 2, Aug. 1955, pp. 196-203.
Holper et al., Surgery for tricuspid insufficiency: long-term follow-up after De Vega annuloplasty, The Thoracic and Cardiovascular Surgeon, vol. 41, No. 1, Feb. 1993, pp. 1-8.
Jatene, Left Ventricular Aneurysmectomy. Resection or Reconstruction, J Thorac Cardiovasc Surgical, vol. 89, 1985, pp. 321-331.
Kameda et al., Annuloplasty for Severe Mitral Regurgitation Due to Dilated Cardiomyopathy, Ann Thorac Surg., vol. 61, 1996, pp. 1829-1832.
Kay et al., Surgical Treatment of Mitral insufficiency, Surgery, vol. 37, No. 5, May 1955, pp. 697-706.
Kim et al., The Effect of Transvenous Pacemaker and Implantable Cardioverter Defibrillator Lead Placement on Tricuspid Valve Function: An Observational Study, Journal of the American Society of Echocardiography, vol. 21, No. 3, 2008, pp. 284-287.
King et al., Surgery for tricuspid regurgitation late after mitral valve replacement, Circulation, vol. 70, 3 Pt 2, Sep. 1984, pp. I193-I197.
Koniaris et al., Dynamic Retention: A Technique for Closure of the Complex Abdomen in Critically Ill Patients, Archives of Surgery, vol. 136, No. 12, Dec. 2001, pp. 1359-1362.
Kuykendall et al., Surgical Correction of Chronic Mitral Insufficiency in Dogs, Surgery, vol. 44, No. 4, Oct. 1958, pp. 718-725.
Liedtke et al., Functional Reductions in Left Ventricular Volume, Thorac Cardiovasc Surg., vol. 71, No. 2, Feb. 1976, pp. 195-206.
Matsunaga et al., Progression of tricuspid regurgitation after repaired functional ischemic mitral regurgitation, Circulation, vol. 112, Suppl. 9, Aug. 30, 2005, pp. I453-I457.
Matsuyama et al., Predictors of residual tricuspid regurgitation after mitral valve surgery, The Annals of thoracic surgery, vol. 75, No. 6, Jun. 2003, pp. 1826-1828.
McCarthy et al., Tricuspid valve repair: durability and risk factors for failure, The Journal of Thoracic and cardiovascular surgery, vol. 127, No. 3, Mar. 2004, pp. 674-685.
McKenzie et al., Current Concepts in Surgical Correction of Acquired Mitral Insufficiency, Circulation, vol. 28, Oct. 1963, pp. 603-616.
Minale et al., Selective annuloplasty of the tricuspid valve. Two-year experience, The Journal of thoracic and cardiovascular surgery, vol. 99, No. 5, 1990, pp. 846-851.
Moore et al., Unsuitability of Transventricular Autogenous Slings for Diminishing Valvular Insufficiency, Surgery, vol. 33, No. 2, Feb. 1953, pp. 173-182.
Murray et al., Reconstruction of the Valves of the Heart, The Canadian Medical Association Journal, vol. 38, No. 4, Apr. 1938, pp. 317-319.
Nath et al., Impact of tricuspid regurgitation on long-term survival, Journal of the American College of Cardiology, vol. 43, No. 3, Feb. 4, 2004, pp. 405-409.
Paulis et al., The De Vega tricsuspid annuloplasty: perioperative mortality and long term follow-up, J Cardiovasc Surg (Torino), vol. 31, 1990, pp. 512-517.
Peltola et al., De Vega's annuloplasty for tricuspid regurgitation, Annales chirurgiae et gynaecologiae, vol. 85, No. 1, 1996, pp. 40-43.
Rankin et al., A Clinical Comparison of Mitral Valve Repair Versus Vaive Replacement in Ischemic Mitral Regurgitation, J Thorne Cardiovasc Surg., vol. 95, No. 2, Feb. 1988, pp. 165-177.
Saab et al., Left Ventricular Aneurysm: A New Surgical Approach, Thorac Cardiovasc Surg., vol. 37, No. 1, Feb. 1989, pp. 11-19.
Sakakibara, A Surgical Approach to the Correction of Mitral Insufficiency, Annals of Surgery. vol. 142, No. 2, Aug. 1955, pp. 196-203.
Salati et al., Severe Diastolic Dysfunction after Endoventriculoplasty, J Thorac Cardiovasc Surg., vol. 109, No. 4, Apr. 1995, pp. 694-701.

(56) References Cited

OTHER PUBLICATIONS

Scully et al., Tricuspid valve replacement. Fifteen years of experience with mechanical prostheses and bioprostheses, J of Thoracic and Card. Surg., vol. 109, No. 6, Jun. 1995, pp. 1035-1041.

Singh et al., Midterm outcomes of tricuspid valve repair versus replacement . . . , The Annals of Thoracic Surgery, vol. 82, No. 5, Nov. 2006, pp. 1735-1741.

Skillington et al., Surgical Treatment for Infarct-Related Ventricular Septal Defects . . . , J Thorac Cardiovasc Surg., vol. 99, No. 5, May 1990, pp. 798-808.

Sosa et al., Recurrent Ventricular Tachycardia Associated With Postinfarction Aneurysm. Results of Left Ventricular . . . , J Thorac Cardiovasc Surg., vol. 103, No. 5, May 1992, pp. 855-860.

Tang et al., Tricuspid valve repair with an annuloplasty ring results in improved long-term outcomes, Circulation, vol. 114, Suppl. 1, Jul. 4, 2006, pp. I577-I581.

Tashiro et al., Extended Endocardia! Repair of Postinfarction Ventricular Septal Rupture: New Operative Technique-Modification . . . , J Card Surg., vol. 9, No. 2, Mar. 1994, pp. 97-102.

Tei et al., The tricuspid valve annulus: study of size and motion . . . , Circulation, vol. 114, Suppl 1, Jul. 4, 2006, pp. I492-I498.

Templeton ILL et al., Experimental Reconstruction of Cardiac Valves by Venous and Pericardia! Grafts, Annals of Surgery vol. 129, No. 2, Feb. 1949, pp. 161-176.

Wilson, Studies in Experimental Mitral Obstruction in Relation to the Surgical Treatment of Mitral Stenosis, The British, Journal of Surgery, vol. XVIII, No. 70, pp. 259-274.

Yacoub et al., Anatomic Correction of the Syndrome of Prolapsing Right Coronary Aortic Cusp, Dilatation of the Sinus . . . , J Thorac Cardiovasc Surg., vol. 113, No. 2, Feb. 1997, pp. 253-260.

DEVICES, SYSTEMS, AND METHODS FOR RESHAPING A HEART VALVE ANNULUS

RELATED APPLICATIONS

This application claims the benefit of U.S. Provisional Application Ser. No. 62/131,688 filed 11 Mar. 2015.

FIELD OF THE INVENTION

The invention is directed to devices, systems, and methods for improving the function of a heart valve, e.g., in the treatment of tricuspid valve regurgitation.

BACKGROUND OF THE INVENTION

I. The Anatomy of a Healthy Heart

The heart (see FIG. 1) is slightly larger than a clenched fist. It is a double (left and right side), self-adjusting muscular pump, the parts of which work in unison to propel blood to all parts of the body. The right side of the heart receives poorly oxygenated ("venous") blood from the body from the superior vena cava and inferior vena cava and pumps it through the pulmonary artery to the lungs for oxygenation. The left side receives well-oxygenation ("arterial") blood from the lungs through the pulmonary veins and pumps it into the aorta for distribution to the body.

The heart has four chambers, two on each side—the right and left atria, and the right and left ventricles. The atriums are the blood-receiving chambers, which pump blood into the ventricles. The ventricles are the blood-discharging chambers. A wall composed of fibrous and muscular parts, called the interatrial septum separates the right and left atriums (see FIGS. 2 to 4). The fibrous interatrial septum is, compared to the more friable muscle tissue of the heart, a more materially strong tissue structure in its own extent in the heart.

An anatomic landmark on the interatrial septum is an oval, thumbprint sized depression called the oval fossa, or fossa ovalis (shown in FIG. 4), which is a remnant of the oval foramen and its valve in the fetus. It is free of any vital structures such as valve structure, blood vessels and conduction pathways. Together with its inherent fibrous structure and surrounding fibrous ridge which makes it identifiable by angiographic techniques, the fossa ovalis is the favored site for trans-septal diagnostic and therapeutic procedures from the right into the left heart, and attachment of structure to heart tissue. Before birth, oxygenated blood from the placenta was directed through the oval foramen into the left atrium, and after birth the oval foramen closes.

The synchronous pumping actions of the left and right sides of the heart constitute the cardiac cycle. The cycle begins with a period of ventricular relaxation, called ventricular diastole. The cycle ends with a period of ventricular contraction, called ventricular systole.

The heart has four valves (see FIGS. 2 and 3) that ensure that blood does not flow in the wrong direction during the cardiac cycle; that is, to ensure that the blood does not back flow from the ventricles into the corresponding atria, or back flow from the arteries into the corresponding ventricles. The valve between the right atrium and the right ventricle is the tricuspid valve. The valve between the left atrium and the left ventricle is the mitral valve. The pulmonary valve is at the opening of the pulmonary artery. The aortic valve is at the opening of the aorta.

At the beginning of ventricular diastole (i.e., ventricular filling) (see FIG. 2), the aortic and pulmonary valves are closed to prevent back flow from the arteries into the ventricles. Shortly thereafter, the tricuspid and mitral valves open (as FIG. 2 shows), to allow flow from the atriums into the corresponding ventricles. Shortly after ventricular systole (i.e., ventricular emptying) begins, the tricuspid and mitral valves close (see FIG. 3)—to prevent back flow from the ventricles into the corresponding atriums—and the aortic and pulmonary valves open—to permit discharge of blood into the arteries from the corresponding ventricles.

The opening and closing of heart valves occur primarily as a result of pressure differences. For example, the opening and closing of the tricuspid valve occurs as a result of the pressure differences between the right atrium and the right ventricle. During ventricular diastole, when ventricles are relaxed, the return of carbon dioxide rich blood from the superior and inferior vena cava into the right atrium causes the pressure in the atrium to exceed that in the ventricle. As a result, the tricuspid valve opens, allowing blood to enter the ventricle. As the ventricle contracts during ventricular systole, the intraventricular pressure rises above the pressure in the atrium and pushes the tricuspid valve shut.

The tricuspid and mitral valves are defined by fibrous rings of collagen, each called an annulus, which forms a part of the fibrous skeleton of the heart. The annulus provides attachments for the three cusps or leaflets of the tricuspid valve (called the anterior, posterior, and septal leaflets) and the two cusps or leaflets of the mitral valve (called the anterior and posterior leaflets). The leaflets receive chordae tendineae from more than one papillary muscle. In a healthy heart, these muscles and their tendinous chords support the mitral and tricuspid valves, allowing the leaflets to resist the high pressure developed during contractions (pumping) of the left and right ventricles. FIG. 5 shows the chordae tendineae and papillary muscles in the right ventricle that support the tricuspid valve.

As seen in FIGS. 5 and 6, the tricuspid valve complex consists of the three leaflets, chordae tendineae, two main papillary muscles, the tricuspid annulus, and the right atrial and right ventricular myocardium. Successful valve function depends on the integrity and coordination of these components. Of the three tricuspid valve leaflets, the anterior leaflet is generally the largest and the posterior leaflet is notable for the presence of multiple scallops. The anterior papillary muscle provides chordae to the anterior and posterior leaflets. The medial papillary muscle provides chordae to the posterior and septal leaflets. The septal wall gives chordae to the anterior and septal leaflets (note that there is no formal septal papillary muscle as with the anterior and posterior papillary muscles). The small septal wall leaflet is fairly fixed and there is little room for compensation/movement if the free wall of right ventricle/tricuspid annulus should dilate.[2] Dilation of the tricuspid annulus therefore primarily occurs in the anterior/posterior (mural) aspect (see FIG. 7).[3]

Other important factors influencing the degree of tricuspid regurgitation include the right ventricular preload, afterload and right ventricular function. The tricuspid annulus is dynamic and there is approximately a nineteen percent reduction in annular circumference (approximately thirty percent reduction in annular area) with atrial systole.[4, 5]

A 3-dimensional (3D) echocardiographic study has shown that the tricuspid annulus has a complicated 3D geometry (see FIG. 8), distinct from the simpler "saddle shape" of the mitral annulus. In patients with functional tricuspid regurgitation, the tricuspid annulus is generally more dilated in the septal-lateral direction, resulting in a more circular shape than in healthy subjects.[4]

As FIGS. 2 and 3 show, the anterior portion of the mitral valve annulus is intimate with the non-coronary leaflet of the aortic valve. As FIGS. 2 and 3 also show, the mitral valve annulus is also near other critical heart structures, such as the circumflex branch of the left coronary artery (which supplies the left atrium, a variable amount of the left ventricle, and in many people the SA node) and the AV node (which, with the SA node, coordinates the cardiac cycle).

Also in the vicinity of the posterior mitral valve annulus is the coronary sinus and its tributaries. These vessels drain the areas of the heart supplied by the left coronary artery. The coronary sinus and its tributaries receive approximately 85% of coronary venous blood. The coronary sinus empties into the posterior of the right atrium, anterior and inferior to the fossa ovalis (see FIG. 4). A tributary of the coronary sinus is called the great cardiac vein, which courses parallel to the majority of the posterior mitral valve annulus, and is superior to the posterior mitral valve annulus by an average distance of about 9.64+/−3.15 millimeters (Yamanouchi, Y, Pacing and Clinical Electrophysiology 21(11):2522-6; 1998).

II. Characteristics and Causes of Tricuspid Valve Dysfunction

When the left ventricle contracts after filling with blood from the left atrium, the walls of the ventricle move inward and release some of the tension from the papillary muscle and chords. The blood pushed up against the under-surface of the mitral leaflets causes them to rise toward the annulus plane of the mitral valve. As they progress toward the annulus, the leading edges of the anterior and posterior leaflet come together forming a seal and closing the valve. In the healthy heart, leaflet coaptation occurs near the plane of the mitral annulus. The blood continues to be pressurized in the left ventricle until it is ejected into the aorta. Contraction of the papillary muscles is simultaneous with the contraction of the ventricle and serves to keep healthy valve leaflets tightly shut at peak contraction pressures exerted by the ventricle.

In a healthy heart (see FIG. 9), the dimensions of the tricuspid valve annulus create an anatomic shape and tension such that the leaflets coapt, forming a tight junction, at peak contraction pressures. Where the leaflets coapt at opposing sides of the annulus are called the leaflet commissures.

Valve malfunction can result from the chordae tendineae (the chords) becoming stretched, and in some cases tearing. When a chord tears, the result is a leaflet that flails. Also, a normally structured valve may not function properly because of an enlargement of or shape change in the valve annulus, as shown in FIG. 7. This condition is referred to as a dilation of the annulus and generally results from heart muscle failure. In addition, the valve may be defective at birth or because of an acquired disease.

Regardless of the cause, tricuspid valve dysfunction can occur when the leaflets do not coapt at peak contraction pressures (see FIG. 10). As shown, the coaptation line of the three leaflets is not tight at ventricular systole. As a result, an undesired back flow of blood from the right ventricle into the right atrium can occur.

The general causes of tricuspid valve pathology are secondary (74%), rheumatic (11%), congenital (9%), or other (endocarditis, leaflet tear/prolapse, chordal rupture, papillary muscle rupture [rare], or myxomatous degeneration of the tricuspid valve).[6] In North America, the most common cause of tricuspid valve disease is tricuspid regurgitation (TR) secondary to left heart pathology, such as mitral valve disease/regurgitation and left heart failure.[7] This is felt to result in right-sided pressure overload which results in right ventricular chamber enlargement, tricuspid annular dilation, and resultant TR. This mechanistic cascade led to the concept that treatment of the left-sided abnormality will result in secondary improvement or amelioration of TR. However, Dreyfus et al. have made the point that because this paradigm advocates treatment of proposed "primary" lesion only (i.e., mitral valve disease), this approach will not directly correct tricuspid annular dilation or right ventricular function, the major determinants of functional TR.

Without treatment, TR may become worse over time leading to severe symptoms, biventricular heart failure and death.[8] It has been shown in a large retrospective echocardiographic analysis of 5223 subjects by Nath et al., that independent of echo-derived pulmonary artery systolic pressure, left ventricular ejection fraction, inferior vena cava size, and right ventricular size and function, survival is worse for patients with moderate and severe TR than for those with no TR (TR graded using Framingham Heart Study criteria).[9] In this series, the prevalence of TR in a Veterans Administration population was: no TR, 11.5%; mild TR, 68.8%; moderate TR, 11.8%; and severe TR, 3.8%.

The prevalence of TR from pacemaker leads is as yet poorly defined, but is likely more significant and prevalent than currently perceived. In a recent report by Kim et al., the effect of transtricuspid permanent pacemaker (PPM) or implantable cardiac defibrillator (ICD) leads on 248 subjects with echocardiograms before and after device placement was studied. The authors found that TR worsened by 1 grade or more after implant in 24.2% of subjects, and that TR worsening was more common with ICDs than PPMs with baseline mild TR or less.[10] Residual and recurrent TR after surgical tricuspid annuloplasty is common and occurs in 14% of patients early after operation for all types of annuloplasty.[8] Five years after successful TV repair, 42% of patients with a pacemaker had severe TR, almost double those without the device. This suggests removing the transtricuspid lead and replacing it with an epicardial lead at the time of TV surgery may reduce late repair failure.[1]

There are numerous reports describing the presence of TR in patients undergoing surgery for mitral regurgitation. The prevalence of TR in the postoperative period depends to some degree on the mechanism of MR. Matsuyama et al. reported in a study of 790 patients that only 16% of patients who underwent nonischemic (i.e., degenerative) mitral valve surgery without tricuspid valve surgery developed 3 to 4+ TR at 8 year follow-up.[11] Conversely, TR appears to be prevalent in patients undergoing mitral valve repair for functional ischemic mitral regurgitation. In the series by Matsunaga et al., of 70 patients undergoing MV repair for functional ischemic mitral regurgitation, 30% (21/70) of patients had at least moderate TR before surgery. In the postoperative period, the prevalence of at least moderate TR increased over time from 25% at less than one year, 53% at 1 to 3 year, and 74% at greater than 3 year follow-up.[12]

Significant tricuspid valve insufficiency may also contribute to a poor hemodynamic result even after successful mitral valve repair. In one early series by King et al., patients requiring subsequent tricuspid valve surgery after MV surgery had high early and late mortality. The authors encouraged a policy of liberal use of tricuspid annuloplasty at initial mitral valve surgery.[13] Accordingly, 50-67% of patients undergoing surgery for mitral valve disease have been reported to undergo concomitant surgical TV repair or replacement.[1,6] Investigators have also attempted to identify specific patient subsets that should have TV repair/replacement at the time of MV repair/replacement.

It has been proposed that at the time of MV repair, the presence of tricuspid annular dilation (≥70 mm measured intraoperatively) even in the absence of significant TR should be an indication for TV annuloplasty. This paper also showed that TR increased by at least 2 grades in 45% of the patients who received isolated MVR, supporting the notion that tricuspid dilation is an ongoing, progressive process that often warrants preemptive surgical treatment.[14]

In the series by Singh and colleagues, tricuspid valve repair appears to result in improved mid-term survival (up to 10 years after surgery, primarily due to higher perioperative mortality with replacement) as compared with TV replacement, although there was no difference in valve-related mortality or need for TV reoperation.) The authors hypothesized that the higher perioperative mortality with replacement may have been due to a rigid object (TV valve) in a deformable low-pressure cavity (right ventricle, RV), with resultant RV dysfunction and perioperative low output state. Although patients in this series had less recurrent TR with replacement vs. repair (95% vs. 62% had mild or less TR at most recent echocardiographic follow-up), there was no difference in functional class in either group.

Other surgical series have shown that successful tricuspid valve repair (primarily when combined with other valve surgeries) resulted in a significant improvement in recurrent TR, survival, and event-free survival.

III. Prior Treatment Modalities

Multiple percutaneous therapies are now available or under development for the treatment of aortic, mitral and pulmonic valve disease. In contrast, there has been little discussion regarding percutaneous approaches to tricuspid valve repair. Despite the fact that tricuspid regurgitation (TR) can result in significant symptoms, it is rare for patients to be referred for isolated surgical tricuspid valve repair given the morbidity and mortality of surgery.

The presence of tricuspid regurgitation is often underdiagnosed and surgically ignored. Re-operations for recurrent TR are also felt to be high risk surgical procedures (~37% in-hospital mortality) and are therefore not offered to many patients.[1] In this era of percutaneous valve repair and replacement, the relevance and potential need for the percutaneous treatment of TR should be considered.

The need remains for a simple, cost effective, and less invasive devices, systems, and methods for treating dysfunction of a heart valve, e.g., in the treatment of tricuspid valve regurgitation.

SUMMARY OF THE INVENTION

The invention comprises devices, systems, and methods for reshaping a heart valve annulus.

One aspect of the invention provides a method of placing an implant within a heart chamber. The method can comprise deploying a guide wire in an intravascular path that extends from a first vascular access into a heart chamber and from the heart chamber to a second vascular access site different than the first vascular access site, the guide wire having a first end extending beyond the first vascular access site and a second end extending beyond the second vascular access site, coupling the implant to one end of the guide wire, and pulling on the other end of the guide wire to pull the implant along at least a portion of the intravascular path into the heart chamber.

The method may include placing the implant in tension within the heart chamber. In one embodiment, the heart chamber can comprise the right atrium. The implant may comprise, for example, a metallic material or polymer material or a metallic wire form structure or a polymer wire form structure or suture material or equine pericardium or porcine pericardium or bovine pericardium or preserved mammalian tissue.

Another aspect of the invention provides a system comprising an implant sized and configured for placement within a heart chamber, a guide wire sized and configured for deployment in an intravascular path that extends from a first vascular access into the heart chamber and from the heart chamber to a second vascular access site different than the first vascular access site, the guide wire having a first end extending beyond the first vascular access site and a second end extending beyond the second vascular access site, and a connector to connect an end of the implant to one end of the guide wire such that pulling on the other end of the guide wire pulls the implant along at least a portion of the intravascular path into the heart chamber. The bridge element may comprise, for example, a metallic material or polymer material or a metallic wire form structure or a polymer wire form structure or suture material or equine pericardium or porcine pericardium or bovine pericardium or preserved mammalian tissue.

Other features and advantages of the invention shall be apparent based upon the accompanying description, drawings, and claims.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

I. Trans-Annular Implants for Direct Shortening of Selected Dimensions of a Heart Valve Annulus A. Implant Configurations FIGS. 11A to 11G show various embodiments of an implant 10 that is sized and configured to extend across or through portions of the right atrium, thereby spanning and/or affecting the tricuspid valve annulus to allow shortening of selected trans-annular dimensions.

The implant 10 comprises a spanning region or bridging element 12 having at least a first bridge stop region and a second bridge stop region, which can comprise a variety of locations. Tensioning the bridging element would result in a reduction of trans-annular dimensions and improved leaflet coaption with consequent tricuspid regurgitation reduction.

1. Bridging Element

In its most basic form, the bridge 12 is made from a biocompatible metallic or polymer material, or a metallic or polymer material that is suitably coated, impregnated, or otherwise treated with a material to impart biocompatibility, or a combination of such materials. The material is also desirably radio-opaque or incorporates radio-opaque features to facilitate fluoroscopic visualization.

The bridge 12 can be formed by bending, shaping, joining, machining, molding, or extrusion of a metallic or polymer wire form structure, which can have flexible or rigid, or inelastic or elastic mechanical properties, or combinations thereof. Alternatively, the bridge 12 can be formed from metallic or polymer thread-like or suture material. Materials from which the bridge 12 can be formed include, but are not limited to, stainless steel, Nitinol, titanium, silicone, plated metals, Elgiloy™, NP55, and NP57.

The bridge 12 can take various shapes and have various cross-sectional geometries. The bridge 12 can have, e.g., a generally curvilinear (i.e., round or oval) cross-section, or a generally rectilinear cross section (i.e., square or rectangular), or combinations thereof. Shapes that promote laminar flow and therefore reduce hemolysis are contemplated, with features such as smoother surfaces and longer and narrower leading and trailing edges in the direction of blood flow.

Figure 1:
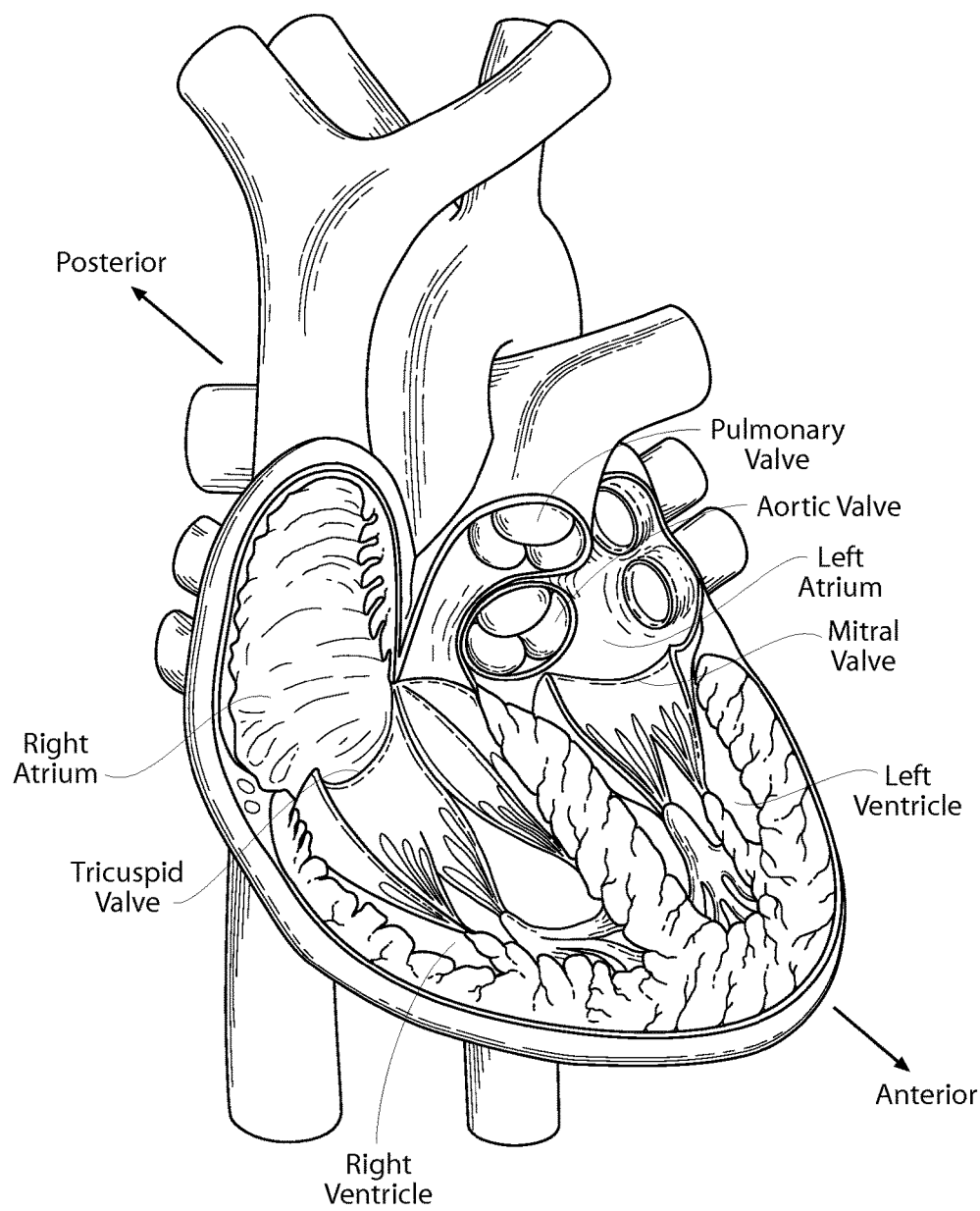
FIG. 1 is an anatomic anterior view of a human heart, with portions broken away and in section to view the interior heart chambers and adjacent structures.
Figure 2:
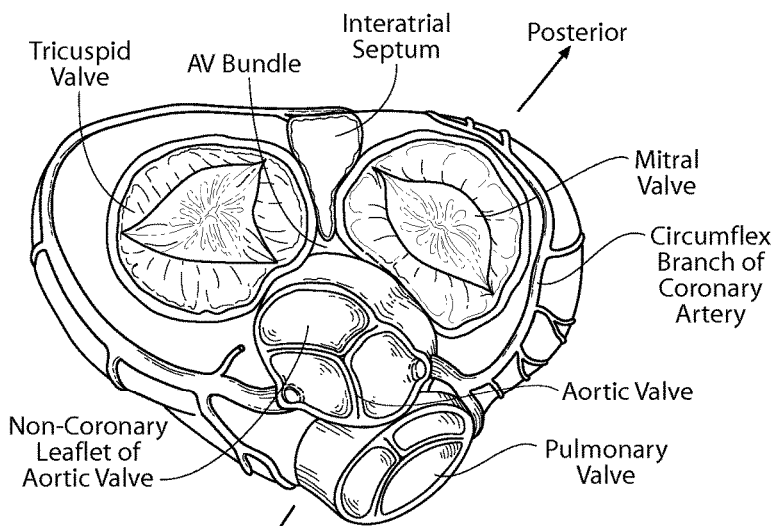
FIG. 2 is an anatomic superior view of a section of the human heart showing the tricuspid valve in the right atrium, the mitral valve in the left atrium, and the aortic valve in between, with the tricuspid and mitral valves open and the aortic and pulmonary valves closed during ventricular diastole (ventricular filling) of the cardiac cycle.
Figure 4:
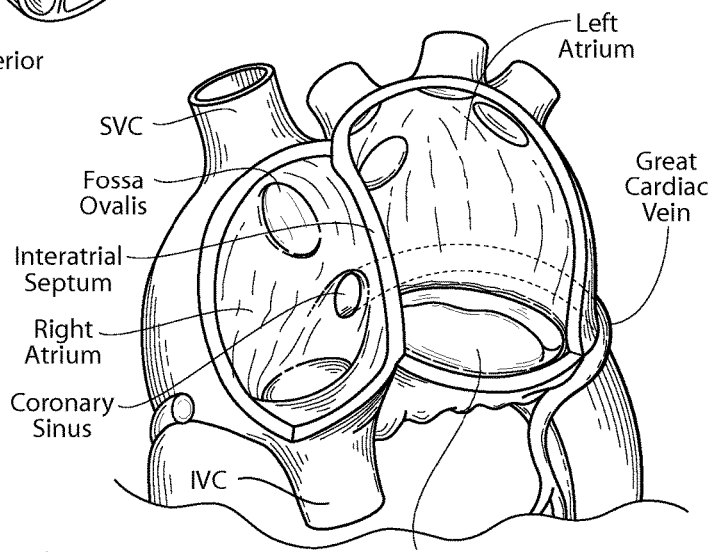
FIG. 4 is an anatomic anterior perspective view of the left and right atriums, with portions broken away and in section to show the interior of the heart chambers and associated structures, such as the fossa ovalis, coronary sinus, and the superior and inferior vena cava.
Figure 3:
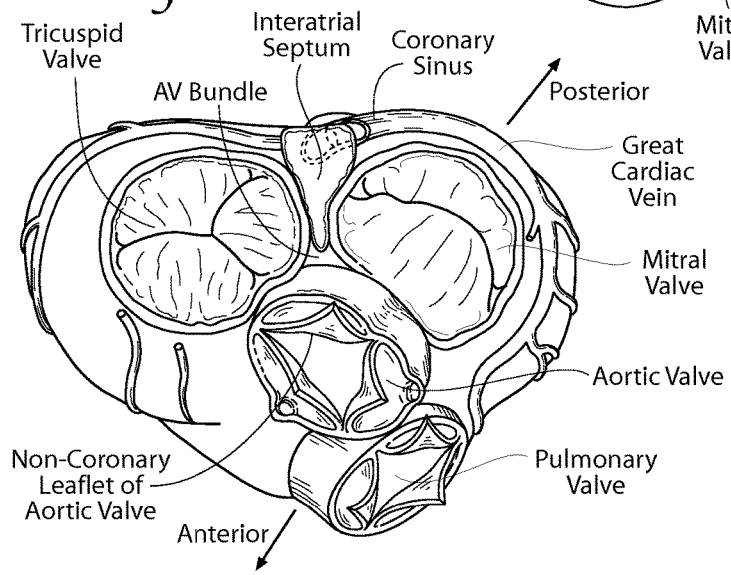
FIG. 3 is an anatomic superior view of a section of the human heart shown in FIG. 2, with the tricuspid and mitral valves closed and the aortic and pulmonary valves opened during ventricular systole (ventricular emptying) of the cardiac cycle.
Figure 5:
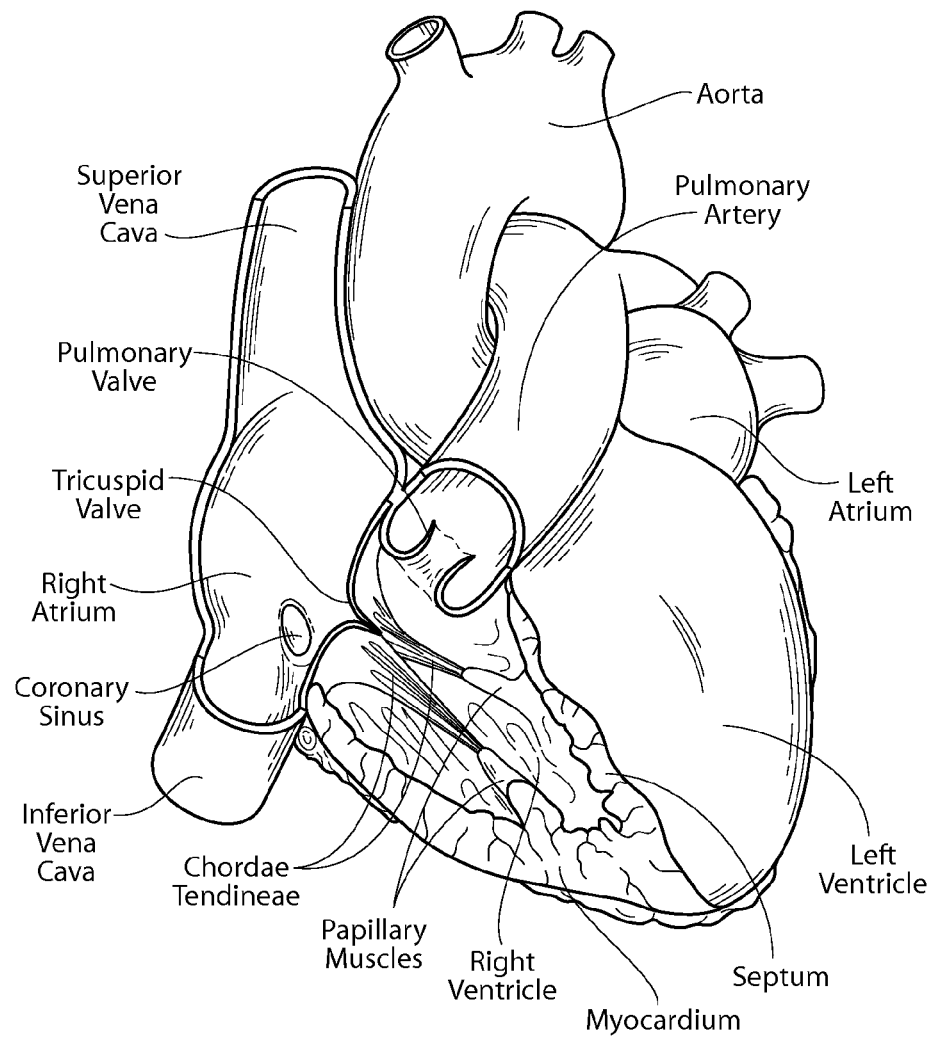
FIG. 5 is an anatomic anterior view of a human heart with portions broken away and in section to show the interior of the right atrium and right ventricle, and associated muscle and chord structures coupled to the tricuspid valve.
Figure 6:
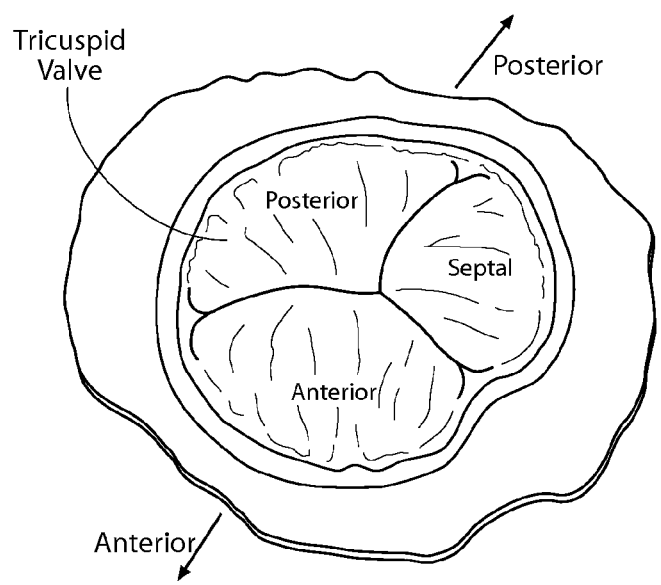
FIG. 6 is a superior view of a healthy tricuspid valve, with the leaflets closed and coapting at peak contraction pressures during ventricular systole.
Figure 7:
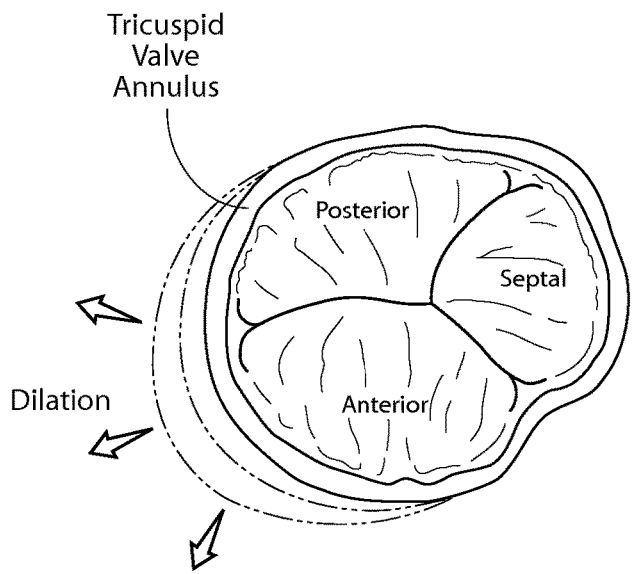
FIG. 7 is a superior view of a dysfunctional tricuspid valve, and showing the common progression of an enlarged and/or dilated annulus, which causes the leaflets to fail to coapt during peak contraction pressures during ventricular systole, leading to tricuspid regurgitation.
Figure 8:
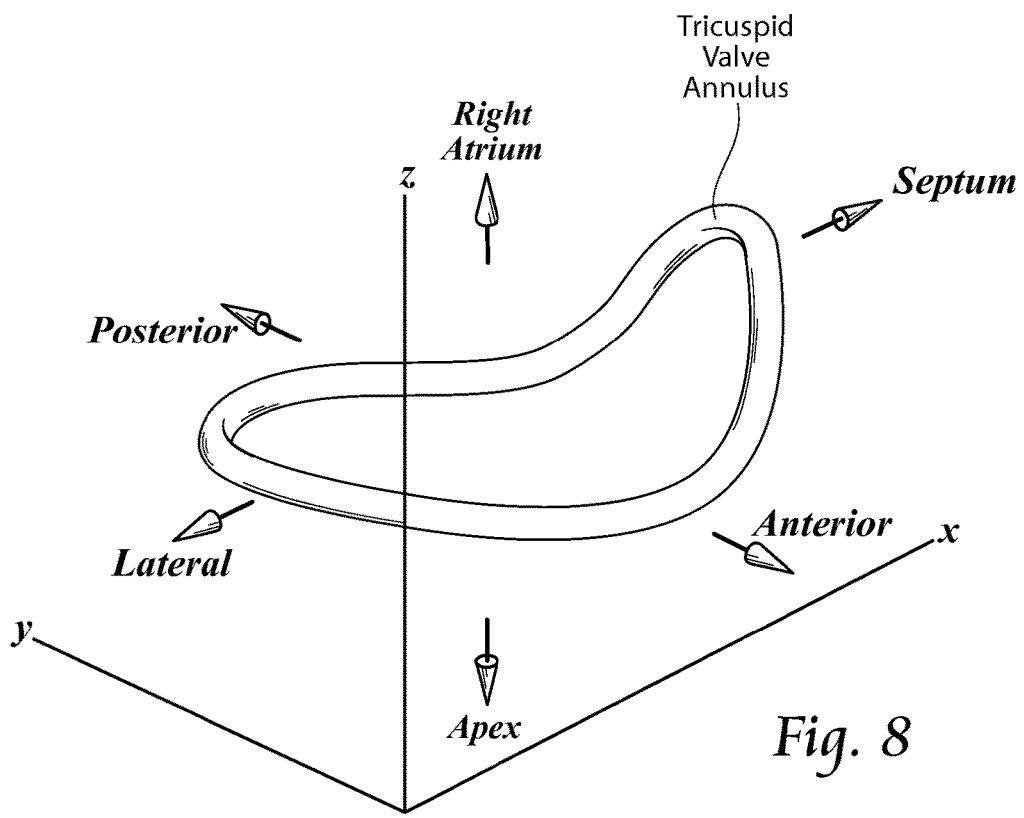
FIG. 8 is a three dimensional view of the tricuspid annulus showing its complicated shape.
Figure 9:
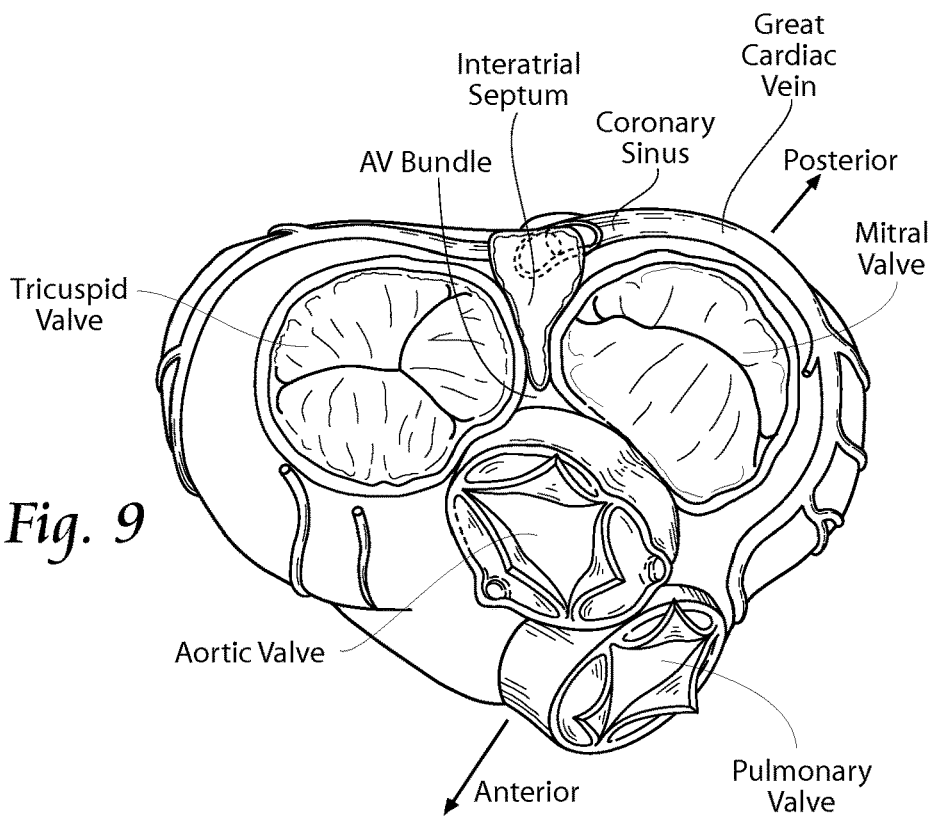
FIG. 9 is an anatomic superior view of a section of the human heart, with the normal tricuspid valve shown in FIG. 6 closed during ventricular systole (ventricular emptying) of the cardiac cycle.
Figure 10:
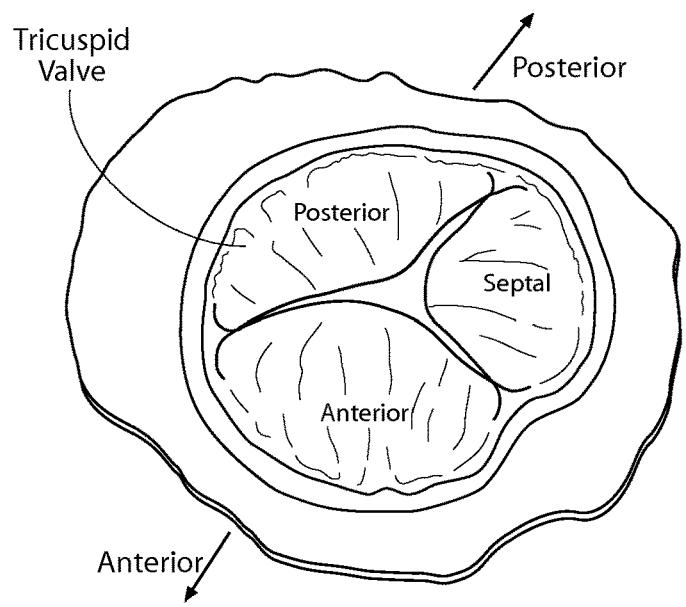
FIG. 10 is a superior view of a dysfunctional tricuspid valve, with the leaflets failing to coapt during peak contraction pressures during ventricular systole, leading to tricuspid regurgitation.

In use, the spanning region or bridging element 12 can be placed into tension between two or more bridge stop regions. The implant 10 thereby serves to apply a direct mechanical force generally in an anterior to posterior direction across the right atrium, although other directions are also possible. The direct mechanical force can serve to shorten the minor axis (line A-P in FIG. 10) of the annulus. In doing so, the implant 10 can also reactively reshape the annulus along its major axis (line S-L in FIG. 10) and/or reactively reshape other surrounding anatomic structures. It should be appreciated, however, the presence of the implant 10 can serve to stabilize tissue adjacent the heart valve annulus, without affecting the length of the minor or major axes.

It should also be appreciated that, when situated in other valve structures, the axes affected may not be the "major" and "minor" axes, due to the surrounding anatomy. In addition, in order to be therapeutic, the implant 10 may only need to reshape the annulus during a portion of the heart cycle, such as during late diastole and early systole when the heart is most full of blood at the onset of ventricular systolic contraction, when most of the tricuspid valve leakage occurs. For example, the implant 10 may be sized to restrict outward displacement of the annulus during late ventricular diastolic relaxation as the annulus dilates.

The mechanical force applied by the implant 10 across the right atrium can restore to the heart valve annulus and leaflets a more normal anatomic shape and tension. The more normal anatomic shape and tension are conducive to coaptation of the leaflets during late ventricular diastole and early ventricular systole, which, in turn, reduces tricuspid regurgitation.

2. Bridge Stop Regions

Bridge stop regions can vary depending on the desired affect on the tricuspid valve annulus. The interatrial septum (A), the inferior vena cava (B), the superior vena cava (C), the right ventricle (D), and the coronary sinus (E) provide practical sites for bridge stop regions, i.e., for the placement of a bridge stop. Each is further described below.

Location of the implant 10 in a supra-annular level within the right atrium, e.g., in the septum and a vena cava, and possibly in the ventricle, not only provides freedom from key vital structure damage or local impingement—e.g., to the right coronary artery, AV node, and the right coronary and non-coronary cusps of the aortic valve—but the supra-annular focused sites are also not reliant on purchase between tissue and direct tension-loaded penetrating/biting/holding tissue attachment mechanisms. Instead, physical structures and force distribution mechanisms such as bridge stops including, for example, stents, T-shaped members, and septal members can be used, which better accommodate the attachment or abutment of mechanical levers and bridge locks, and through which potential tissue tearing forces can be better distributed.

Further, the bridge stop sites do not require the operator to use complex imaging due to radio-opaque bridge stops and well demarcated fluoroscopic landmarks. Adjustment of implant position after or during implantation is also facilitated, free of these constraints. These bridge stop sites also make possible full intra-atrial retrieval of the implant 10.

i. Interatrial Septum

One possible bridge stop region A comprises a posterior bridge stop region which may be adjacent or abutting a region of fibrous tissue in the interatrial septum. As shown, the bridge stop site A is desirably superior to the posterior tricuspid annulus. In the illustrated embodiment, the bridge stop region A is adjacent to or near the inferior rim of the fossa ovalis. Alternatively, the bridge stop region A can be located at a more superior position in the septum, e.g., at or near the superior rim of the fossa ovalis. The bridge stop region A can also be located in a more superior or inferior position in the septum, away from the fossa ovalis, provided that the bridge stop site does not harm the septal tissue region and surrounding structures.

The fibrous tissue in this region provides superior mechanical strength and integrity compared with muscle and can better resist a device pulling through. The septum is the most fibrous tissue structure in its own extent in the heart. Surgically handled, it is usually one of the only heart tissues into which sutures actually can be placed and can be expected to hold without pledgets or deep grasps into muscle tissue, where the latter are required.

ii. Inferior Vena Cava

Another possible bridge stop region B comprises the inferior vena cava. The inferior vena cava B conveys blood to the heart received from the lower half of the body, and terminates near the lower posterior portion of the right atrium. The bridge stop region B provides percutaneous access and presents more tissue mass for obtaining purchase for a bridge stop site.

iii. Superior Vena Cava

Another possible bridge stop region C comprises the superior vena cava. The superior vena cava conveys blood to the heart received from the upper half of the body, and is a short trunk, ranging in length from about two plus inches to about three inches. As with the bridge stop region B, the bridge stop region C also provides percutaneous access and presents more tissue mass for obtaining purchase for a bridge stop site.

iv. Right Ventricle

Yet another possible bridge stop region D comprises the ventricular side of the base of the tricuspid leaflets. This area provides a site where tissue can be readily augmented and consolidated for obtaining purchase for a bridge stop site.

iv. Coronary Sinus

Yet another possible bridge stop region E comprises the coronary sinus. The orifice of the coronary sinus is generally superior to the septal leaflet of the tricuspid valve. The coronary sinus runs transversely in a groove between the left atrium and ventricle on the posterior surface of the heart. The bridge stop region E also provides percutaneous access and presents more tissue mass for obtaining purchase for a bridge stop site.

3. Bridge Stops

It is to be appreciated that a bridge stop as described herein, including a bridge stop adapted for use at bridge stop sites A, B, C, D, and E describes an apparatus that may releasibly hold the bridging element 12 in a tensioned state. The bridge stop(s) may be adapted to allow the bridging element 12 to move independent of the bridge stop sites during a portion of the cardiac cycle when the tension force may be reduced or becomes zero. Alternative embodiments are also described, all of which may provide this function. It is also to be appreciated that the general descriptions of posterior, anterior, superior, and inferior are non-limiting to the bridge stop function or site, i.e., a posterior bridge stop may be used anterior, and an anterior bridge stop may be used posterior.

Bridge stops may be symmetrically shaped or asymmetrically shaped. A symmetrically shaped or asymmetrically shaped bridge stop may be chosen for its use in selecting application of forces differentially and preferentially, i.e, forces or tension on different points along the tricuspid annulus to optimize treatment, such as in cases of malformed or asymmetrical tricuspid valves.

i. Interatrial Septal Bridge Stop

Figure 11A:
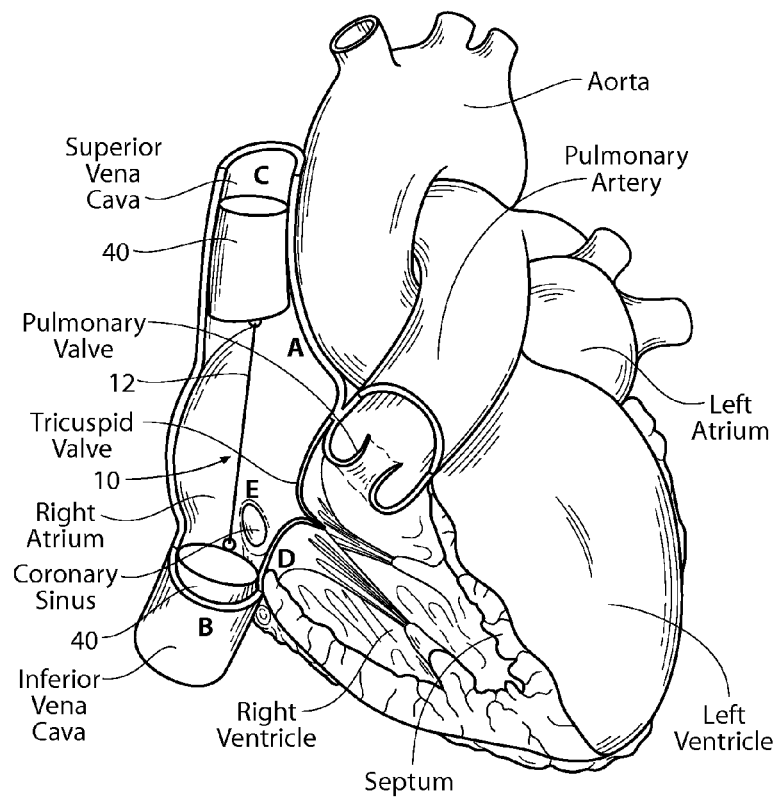
FIG. 11A is anatomic anterior perspective view of the right atrium and right ventricle, with portions broken away and in section to show the presence of an implant system that includes an inter-atrial bridging element that spans the tricuspid valve annulus, with a superior bridge stop positioned in the superior vena cava and an inferior bridge stop positioned in the inferior vena cava, the inter-atrial bridging element extending in an essentially straight path generally across the tricuspid valve.
Figure 11B:
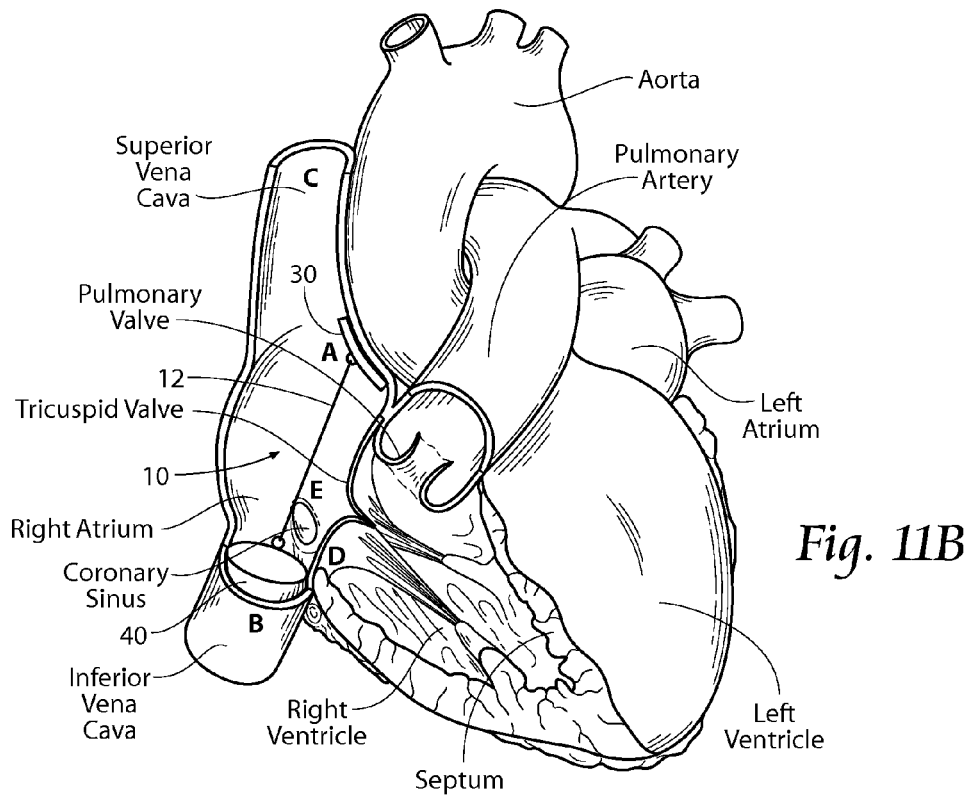
FIG. 11B is anatomic anterior perspective view of the right atrium and right ventricle, with portions broken away and in section to show the presence of an implant system that includes an inter-atrial bridging element that spans the tricuspid valve annulus, with a superior bridge stop positioned on the inter-atrial septum and an inferior bridge stop positioned in the inferior vena cava, the inter-atrial bridging element extending in an essentially straight path generally across the tricuspid valve.
Figure 11C:
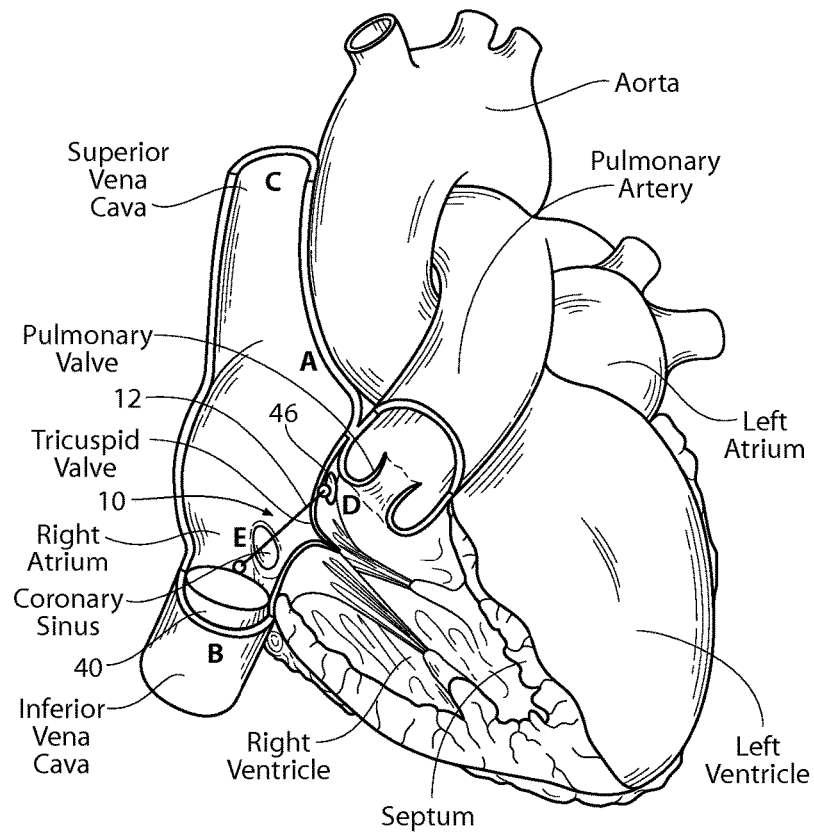
FIG. 11C is anatomic anterior perspective view of the right atrium and right ventricle, with portions broken away and in section to show the presence of an implant system that includes an inter-atrial bridging element that crosses through the base of the leaflet/annulus, with a superior bridge stop positioned on the ventricle side of the tricuspid valve and an inferior bridge stop positioned in the inferior vena cava, the inter-atrial bridging element extending in an essentially straight path through the base of the leaflet/annulus.
Figure 11D:
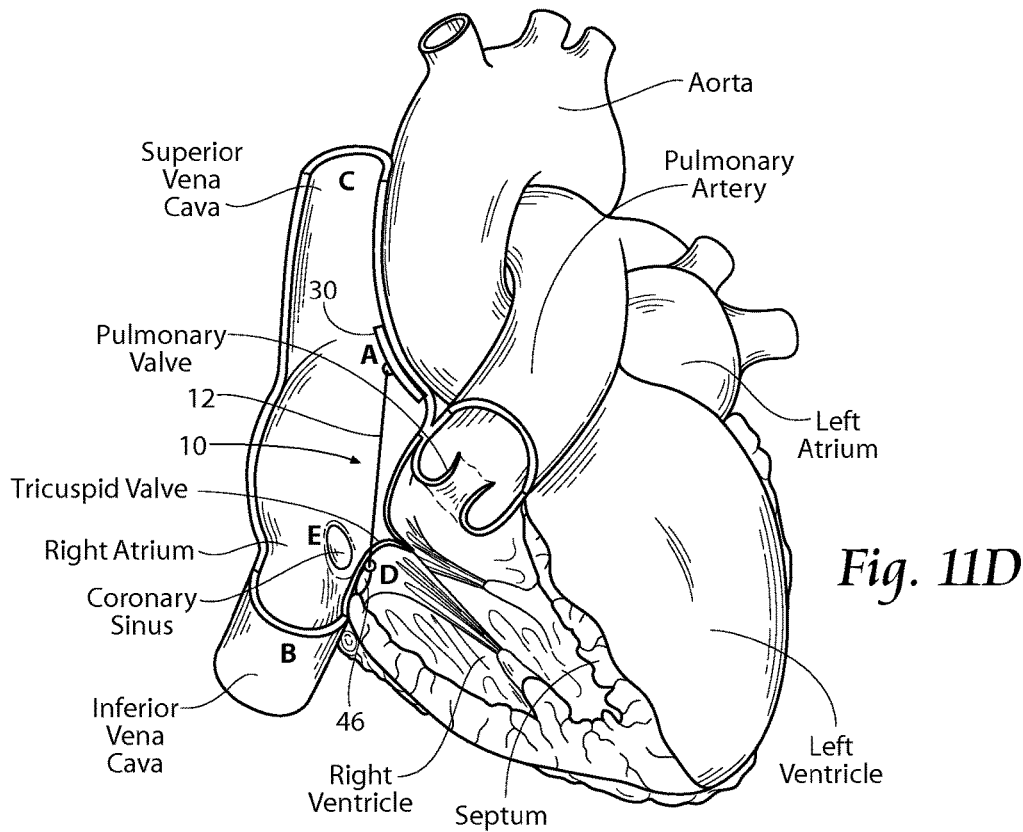
FIG. 11D is anatomic anterior perspective view of the right atrium and right ventricle, with portions broken away and in section to show the presence of an implant system that includes an inter-atrial bridging element that crosses through the base of the leaflet/annulus, with a superior bridge stop positioned on the inter-atrial septum and an inferior bridge stop positioned on the ventricle side of the tricuspid valve, the inter-atrial bridging element extending in an essentially straight path generally through the base of the leaflet/annulus.
Figure 11E:
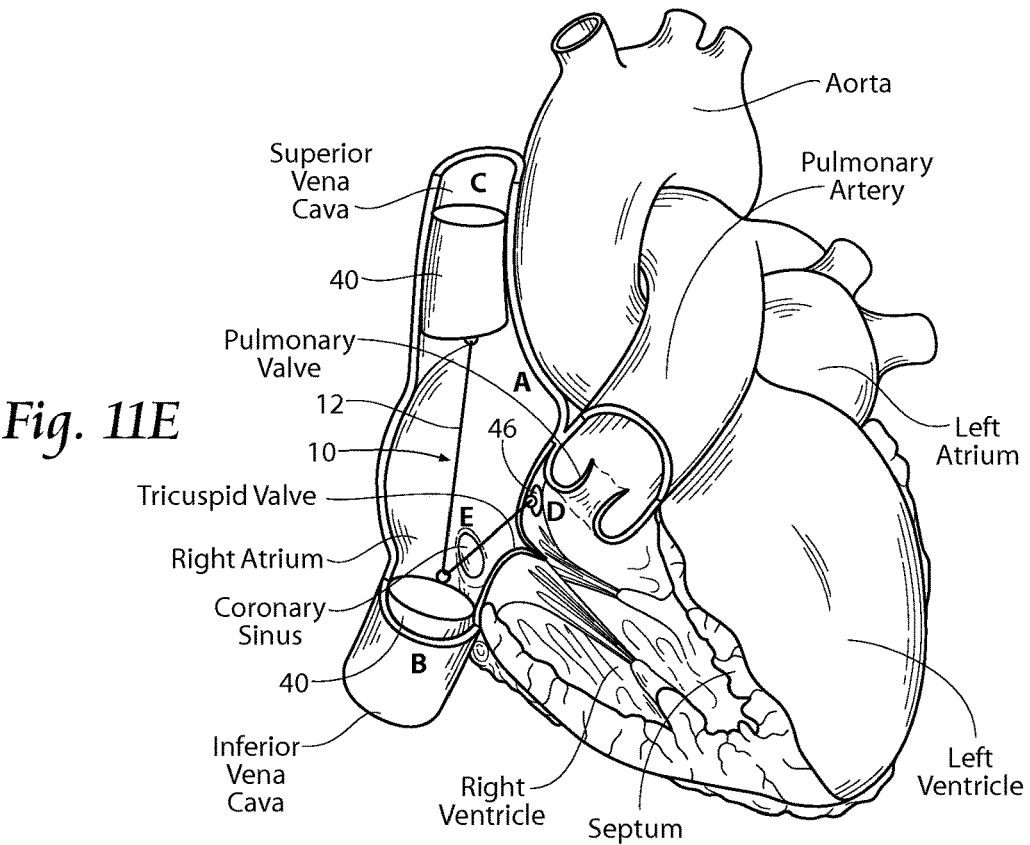
FIG. 11E is anatomic anterior perspective view of the right atrium and right ventricle, with portions broken away and in section to show the presence of an implant system that includes an inter-atrial bridging element that spans the tricuspid valve annulus and crosses through the base of the leaflet/annulus, with a superior bridge stop positioned in the superior vena cava, an inferior bridge stop positioned in the inferior vena cava, and ventricle bridge stop positioned on the ventricle side of the tricuspid valve, the inter-atrial bridging element extending in a generally "V" path from the superior bridge stop to the inferior bridge stop, and from the inferior bridge stop to the ventricle bridge stop.
Figure 11F:
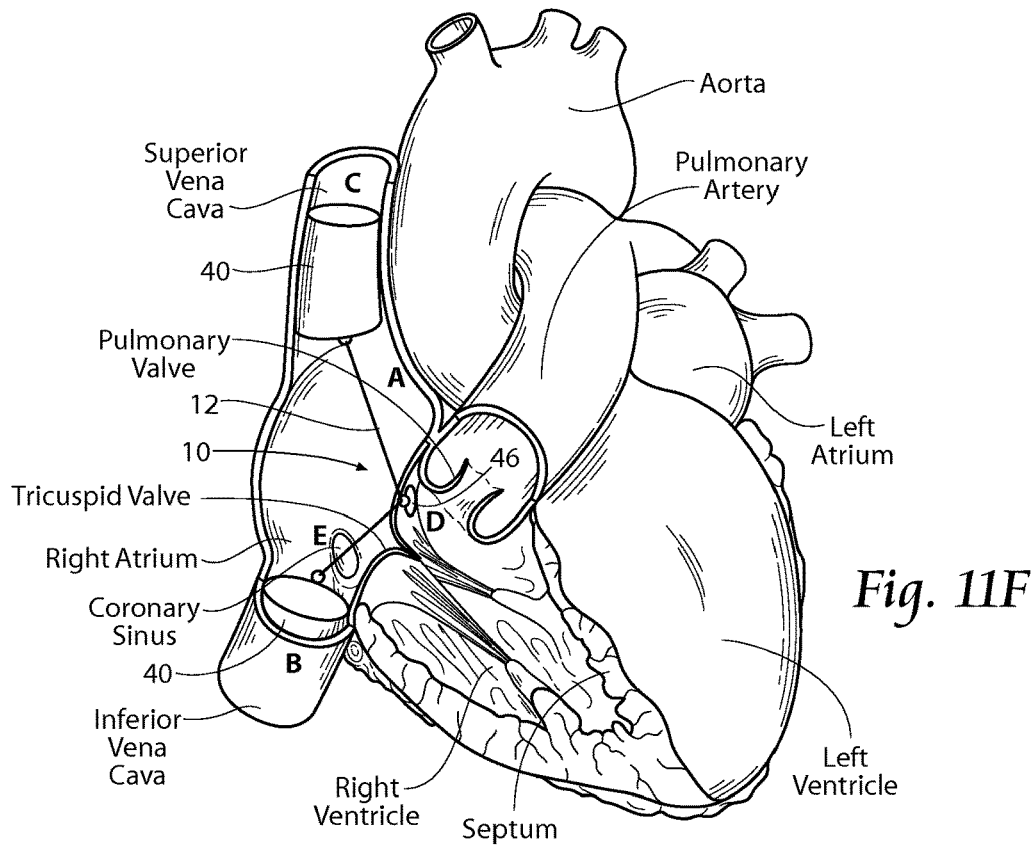
FIG. 11F is anatomic anterior perspective view of the right atrium and right ventricle, with portions broken away and in section to show the presence of an implant system that includes an inter-atrial bridging element that twice crosses through the base of the leaflet/annulus, with a superior bridge stop positioned in the superior vena cava, an inferior bridge stop positioned in the inferior vena cava, and a ventricle bridge stop positioned on the ventricle side of the tricuspid valve, the inter-atrial bridging element extending in a generally "V" path from the superior bridge stop to the ventricle bridge stop, and from the ventricle bridge stop to the inferior bridge stop.
Figure 11G:
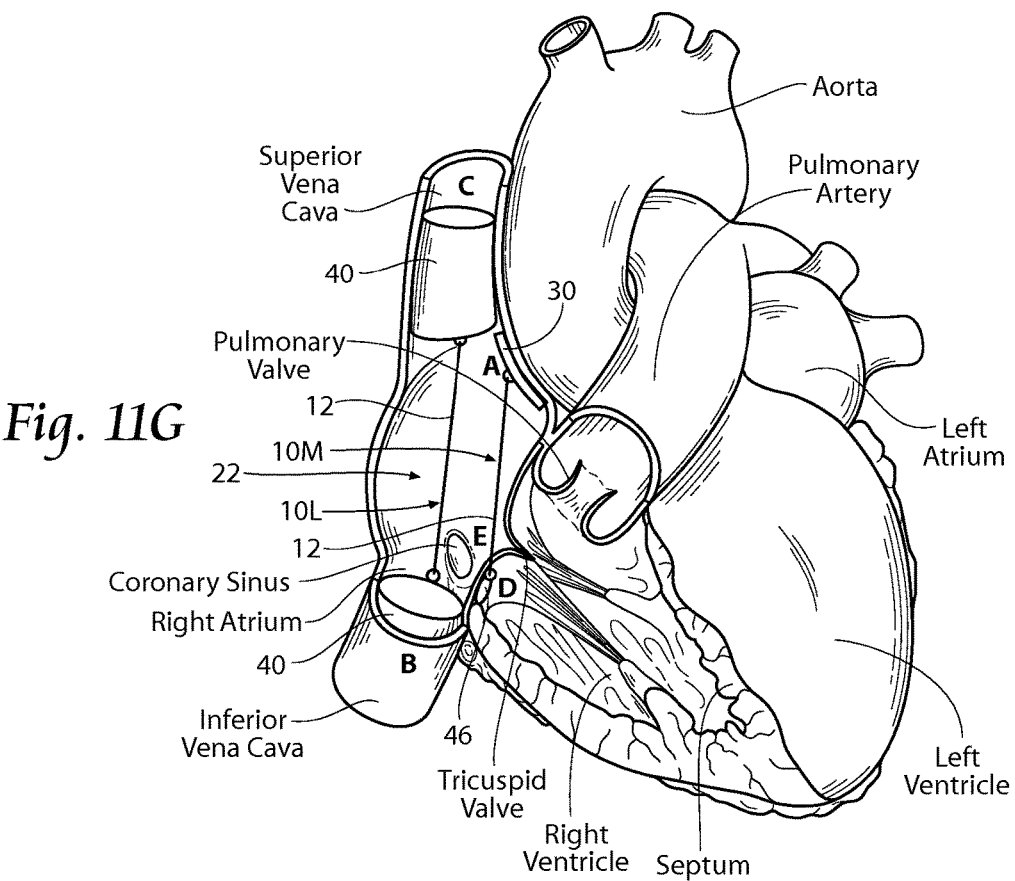
FIG. 11G is anatomic anterior perspective view of the right atrium and right ventricle, with portions broken away and in section to show the presence of an implant system that includes two inter-atrial bridging element that spans the tricuspid valve annulus, with a superior bridge stop positioned in the superior vena cava and an inferior bridge stop positioned in the inferior vena cava, the first inter-atrial bridging element extending in an essentially straight path generally across the tricuspid valve, and a superior bridge stop positioned on the inter-atrial septum and an inferior bridge stop positioned on the ventricle side of the tricuspid valve, the inter-atrial bridging element extending in an essentially straight path generally through the base of the leaflet/annulus.
Figure 12A:
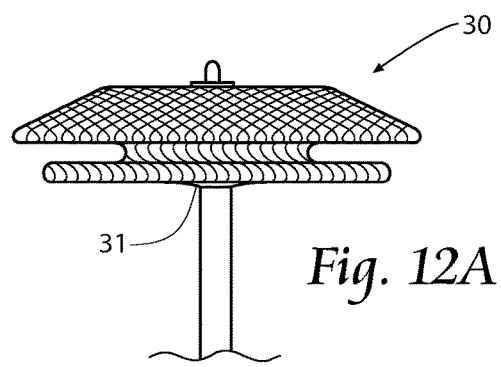
FIG. 12A is a side view of a bridge stop adapted for use in or on the inter-atrial septum, which may be used as part of the implant system of the type shown in FIGS. 11A through 11G.
Figure 12B:
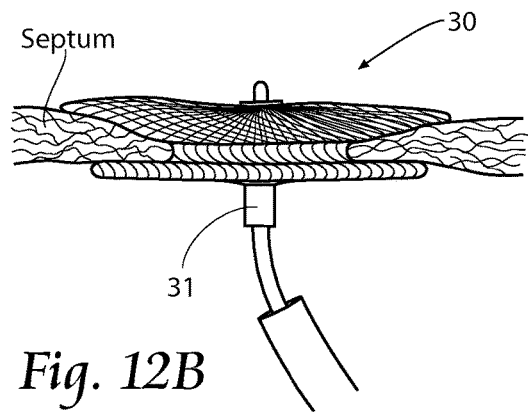
FIG. 12B is a side view of a deployed bridge stop of the type shown in FIG. 12A, showing the bridge stop sandwiching portions of the septum through an existing hole.

The purchase of the posterior bridge stop region A in fibrous interatrial septal tissue is desirably enhanced by one or more septal member(s) 30. FIGS. 11B, 11D, and 11G show the posterior bridge stop region A including the septal member 30. The septal member 30 may be a percutaneously placed expandable tissue and bridging element attachment device, and also may be a commercially available device such as a septal occluder, e.g., Amplatzer® PFO Occluder (see FIGS. 12A and 12B). The septal member 30 may have a small attachment point 31 for the bridge 12 to connect to or to pass through.

The septal member 30 preferably mechanically amplifies the hold or purchase of the posterior bridge stop region A in the fibrous tissue site. The septal member 30 also desirably increases reliance, at least partly, on neighboring anatomic structures of the septum to make firm the position of the implant 10. In addition, the septal member 30 may also serve to plug or occlude a small aperture created in the fossa ovalis or surrounding area during the implantation procedure.

Anticipating that pinpoint pulling forces will be applied by the posterior bridge stop region A to the septum, the forces acting on the septal member 30 should be spread over a moderate area, without causing impingement on valve, vessels or conduction tissues. With the pulling or tensioning forces being transmitted down to the annulus, shortening of the minor axis is achieved.

A flexurally stiff septal member is preferred because it will tend to cause less focal narrowing in the direction of bridge element tension of the right atrium as tension on the bridging element is increased. The septal member 30 should also have a low profile configuration and highly washable surfaces to diminish thrombus formation for devices deployed inside the heart. The septal member may also have a collapsed configuration and a deployed configuration.

ii. Vena Cava Bridge Stop

One or more vena cava bridge stop(s) 40 may be included as part of the implant 10, i.e., an inferior vena cava bridge stop 40 and a superior vena cava bridge stop 40. Both the inferior vena cava bridge stop site B and the superior vena cava bridge stop site C provide a percutaneously accessible and stable site for the placement of a vena cava bridge stop 40. The vena cava bridge stops 40 may be used independently, as seen in FIG. 11A, or in combination with the septal member 30, as seen in FIGS. 11B and 11G.

Figure 13:
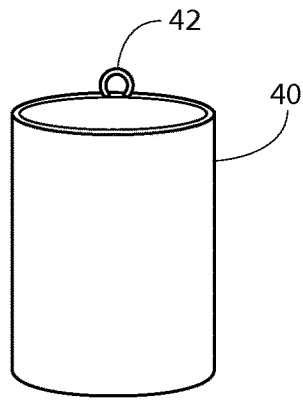
FIG. 13 is a perspective view of a bridge stop configuration adapted for use in the vena cava and/or the coronary sinus, the bridge stop including an attachment point to attach the bridging element to the bridge stop.

A vena cava bridge stop 40 may be a percutaneously placed expandable device and also may be a commercially available device such as a traditional stent 40, as shown in FIG. 13, or it may be of a variety of other configurations or materials. The vena cava bridge stop 40 includes an attachment point 42 to attach the bridging element 12 to the bridge stop.

iii. Ventricle Bridge Stop

One or more ventricle bridge stop(s) 46 may also be included as part of the implant 10, and may be adapted to be placed percutaneously. In this configuration, the implant 10 includes the bridging element 12 crossing through the base of the leaflet/annulus from the ventricular to atrial side, then being attached to one or more of the bridge stops 46 at the bridge stop sites described above. For example, see FIGS. 11C through 11G.

Figure 14A:
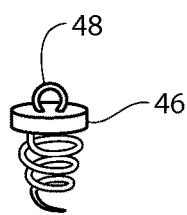
FIG. 14A is a perspective view of a bridge stop configuration adapted for use in the ventricular tissue at or near the tricuspid valve annulus, the bridge stop configuration comprising a cork screw tissue anchor.
Figure 14B:
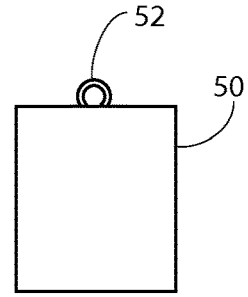
FIG. 14B is a perspective view of an alternative embodiment of a bridge stop configuration adapted for use in the ventricular tissue at or near the tricuspid valve annulus.

The ventricle bridge stop may include multiple configurations (see FIGS. 14A and 14B). As seen in FIG. 14A, the bridge stop 46 comprises a cork screw type of configuration for securement in ventricular tissue at or near the tricuspid annulus. The ventricle bridge stop 46 includes an attachment point 48 to attach the bridging element 12 to the bridge stop. FIG. 14B shows an additional embodiment of a ventricle bridge stop 50 including an attachment point 52.

D. Orientation of the Bridging Element

In the embodiments shown in FIGS. 11A, 11B, and 11G, the implant 10 is shown to span the right atrium beginning at a superior point of focus in the septum or superior vena cava posterior to the approximate mid-point of the tricuspid valve annulus, and proceeding in an inferior direction in a generally straight path directly to the region of anterior focus in the inferior vena cava or right ventricle.

The spanning region or bridging element 12 of the implant 10 may be preformed or otherwise configured to extend in this essentially straight path above the plane of the valve, without significant deviation in depth toward or away from the plane of the annulus, other than as dictated by any difference in depth between the superior and inferior regions of placement.

Lateral or medial deviations and/or superior or inferior deviations in this path can be imparted, if desired, to affect the nature and direction of the force vector or vectors that the implant 10 applies. It should be appreciated that the spanning region or bridging element 12 can be preformed or otherwise configured with various medial/lateral and/or inferior/superior deviations to achieve targeted annulus and/or atrial structure remodeling, which takes into account the particular therapeutic needs and morphology of the patient. In addition, deviations in the path of the bridging element may also be imparted in order to avoid the high velocity blood path within a heart chamber, such as the left atrium.

Regardless of the orientation, more than one implant 10 can be installed to form an implant system 22. For example, FIG. 11G shows a system 22 comprising a lateral implant 10L and a medial implant 10M of a type consistent with the implant 10 as described. FIG. 11G shows the implants 10L and 10M being located at individual superior and inferior bridge stop regions. It should be appreciated that the implants 10L and 10M can also include a common superior or inferior bridge stop region.

II. Supra-Annular Leaflet Treatment of Tricuspid Regurgitation

Figure 15:
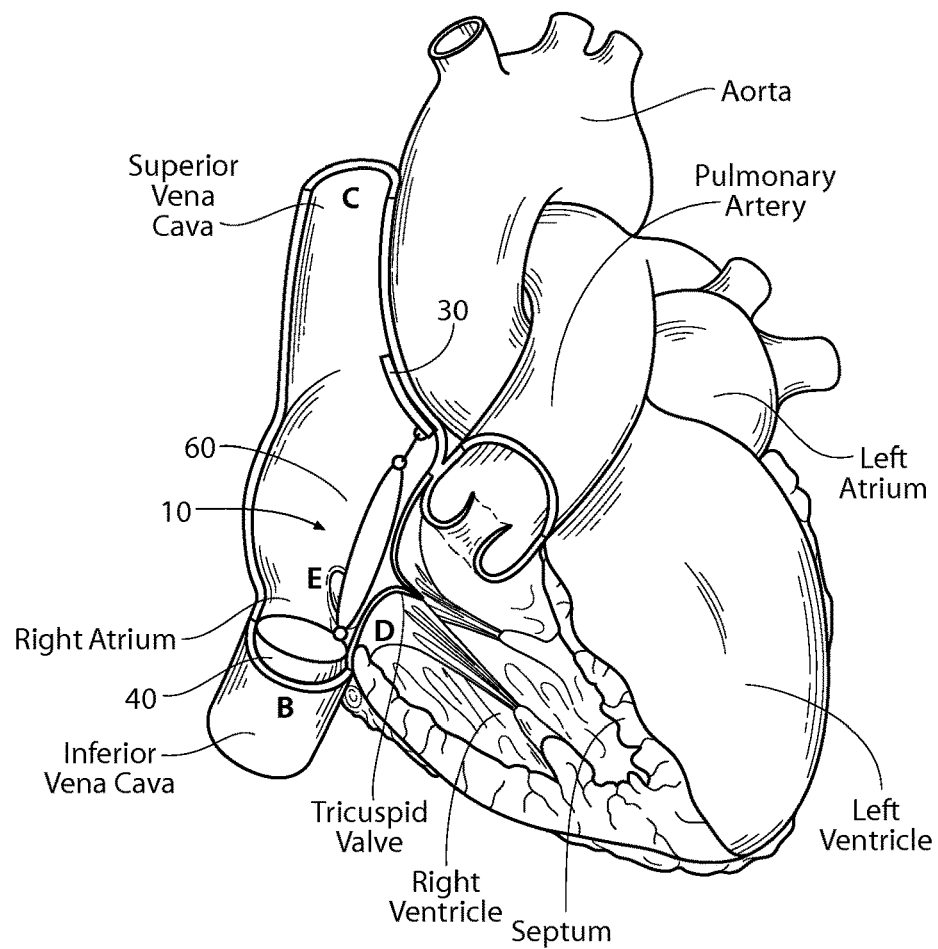
FIG. 15 is anatomic anterior perspective view of the right atrium and right ventricle, with portions broken away and in section to show the presence of an alternative implant system that includes a supra-annular leaflet based device and associated inter-atrial bridging element, the leaflet based device spans the tricuspid valve and allows free passage of blood from the right atrium into the right ventricle during diastole but deflects/stops tricuspid regurgitant flow during systole, the leaflet based device being shown supported by a superior bridge stop positioned on the inter-atrial septum and an inferior bridge stop positioned in the inferior vena cava.

This technique would allow the placement of a leaflet-based device 60 directly above the tricuspid valve (see FIG. 15), which would allow free passage of blood from the right atrium into the right ventricle during diastole but would deflect/stop tricuspid regurgitant flow during systole.

Figure 16A:
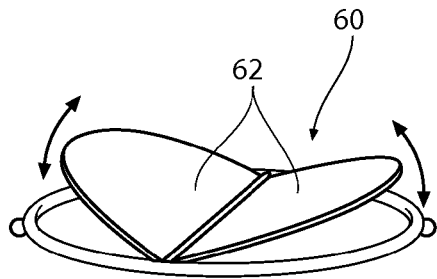
FIG. 16A is a perspective view of a leaflet based device as shown in FIG. 15.
Figure 16B:
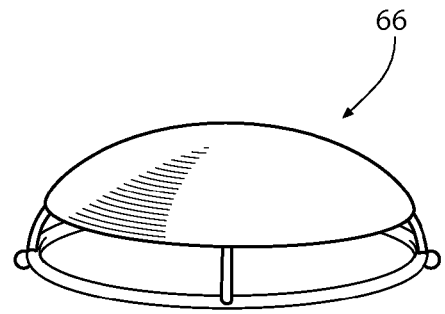
FIG. 16B is a perspective view of an alternative non-leaflet based device that may be used with the system as shown in FIG. 15.
Figure 16C:
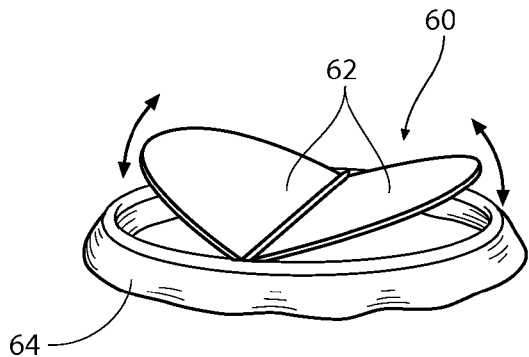
FIG. 16C is a perspective view of an alternative embodiment of a leaflet based device as shown in FIG. 15, the device including a skirt adapted to be coupled to the tricuspid valve annulus to provide a seal around the device.

This device 60 would not replace the existing tricuspid valve, and the native leaflets would remain essentially intact. The device 60 could have moving elements 62, similar to a mechanical or bioprosthetic valve leaflet (see FIG. 16A). Alternately, a device 66 could comprise a generally non-mobile fixed component(s) that would specifically deflect an eccentric regurgitant jet. Either device 60, 66 could be anchored to the tricuspid annulus directly or to one or more bridge stop sites previously described. The supra-annular device 60 could also have a "skirt" 64 or other feature that would attach to the annulus via sutures, for example, and form a seal, making the device more of a true supra-annular valve replacement.

III. Percutaneous Bicuspidalization with Combined Edge-to-Edge Approach

This percutaneous bicuspidalization with combined edge-to-edge approach mimics a surgical technique of bicuspidalization tricuspid annuloplasty for the treatment of functional TR (Ghanta, et al). The surgical technique involves placement of a pledget-supported mattress suture from the anteroposterior commissure to the posteroseptal commissure along the posterior annulus. This technique is based on prior studies by DeLoche et al. that posterior annulus dilation occurs in functional TR and that a focal posterior tricuspid annuloplasty should be effective in most cases.

Figure 17:
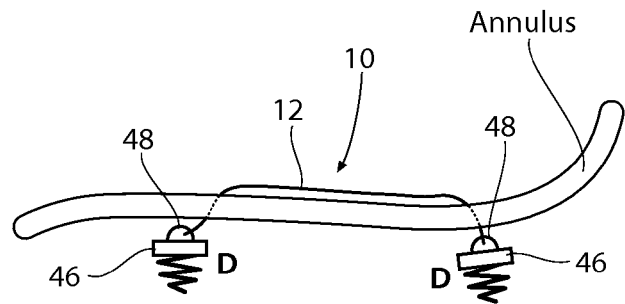
FIG. 17 is anatomic anterior perspective view of the right atrium and right ventricle, with portions broken away and in section to show the presence of an alternative implant system that includes an atrial-ventricle bridging element that crosses through the base of the leaflet/annulus, with at least two bridge stops positioned on the ventricle side of the tricuspid valve, the atrial-ventricle bridging element extending up through the base of the leaflet/annulus from one bridge stop and back down through the base of the leaflet/annulus to the other bridge stop.

The percutaneous approach to this technique involves placement of one or more percutaneously placed anchors 46, for example, that are located on the ventricular side D of the base of the tricuspid leaflets. They will be positioned and placed using catheter techniques, with a connecting bridge 12 crossing through the base of the leaflet/annulus from the ventricular to atrial side. The bridge 12 can be coupled to the other subleaflet anchor and result in partial annuloplasty akin to the surgical procedure (see FIG. 17). It may also be necessary to combine this technique or the aforementioned trans-annular shortening technique with an edge-to-edge leaflet repair, with the selected portions of the leaflets being apposed with suture, clips or other mechanisms (edge to edge for TR described surgically by Castedo et al.) In some cases, an edge-to edge repair approach without annuloplasty may also be effective.

IV. General Methods of System Implantation

The implants 10 or implant systems 22 as just described lend themselves to implantation in a heart or heart chamber in various ways. The implants 10 or implant systems 22 can be implanted, e.g., in an open heart surgical procedure. Alternatively, the implants 10 or implant systems 22 can be implanted using catheter-based technology via a peripheral venous access site, such as in the femoral or jugular vein (via the inferior vena cava and/or superior vena cava) under image guidance (see FIGS. 18A and 18B.

Alternatively, the implants 10 or implant systems 22 can be implanted using thoracoscopic means through the chest, or by means of other surgical access to the right atrium, also under image guidance. Image guidance includes but is not limited to fluoroscopy, ultrasound, magnetic resonance, computed tomography, or combinations thereof.

The implants 10 or implant systems 22 may comprise independent components that are assembled within the body to form an implant, or alternatively, independent components that are assembled exterior the body and implanted as a whole.

Figure 18A:
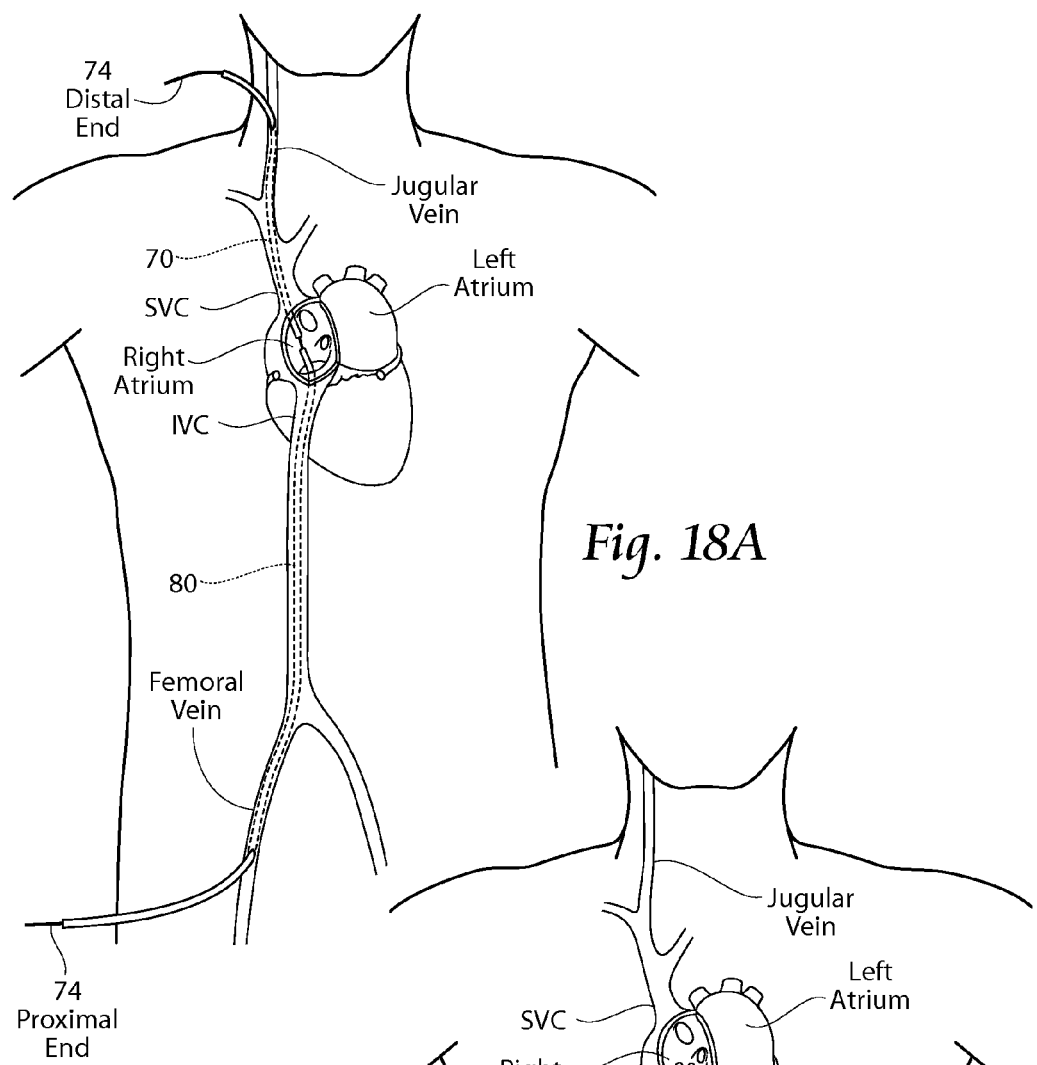
FIG. 18A is an anatomic partial view of a patient depicting multiple access points available for use during implantation of an implant system, and also showing a loop guide wire accessible exterior the body at two locations.
Figure 18B:
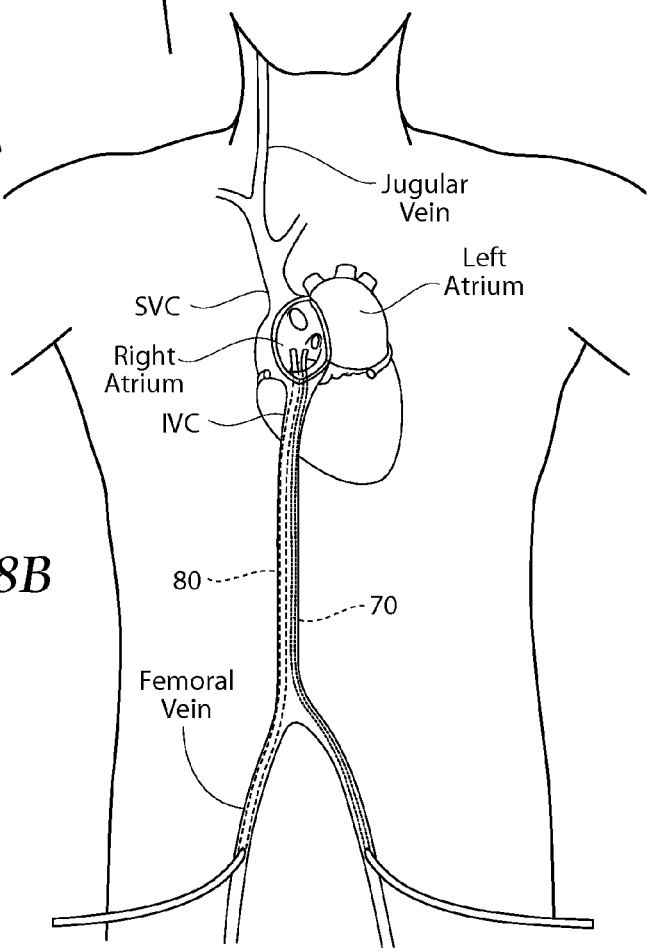
FIG. 18B is an anatomic partial view of a patient depicting multiple access points available for use during implantation of an implant system similar to FIG. 18A, and showing the use of a first catheter and a second catheter access through the left and right femoral veins.

Catheter access to the right atrium can be achieved through either a femoral vein to inferior vena cava or superior vena cava route or an upper extremity or neck vein to SVC or inferior vena cava route. In the case of the superior vena cava, the easiest access is from the upper extremity or neck venous system; however, the inferior vena cava can also be accessed by passing through the superior vena cava and right atrium. Similarly the easiest access to the inferior vena cava is through the femoral vein; however the superior vena cava can also be accessed by passing through the inferior vena cava and right atrium. FIG. 18A shows access through both a superior vena cava route and an inferior vena cava route, and includes a loop guide wire. FIG. 18B shows access through both the left femoral vein and the right femoral vein, without the loop guide wire. It is to be appreciated that other access configurations are possible.

By way of example, FIG. 18A shows a representative embodiment of the deployment of an implant 10 of the type shown in FIG. 11A by a percutaneous, catheter-based procedure, under image guidance. Percutaneous vascular access is achieved by conventional methods into the femoral or jugular vein, or a combination of both (as shown). Under image guidance, a loop guide wire 74 is first passed through the vasculature and includes a distal end and a proximal end, both available external the body. A first catheter 70 and a second catheter 80 are then steered over the guide wire and through the vasculature into the right atrium. It may be a function of the first catheter 70 and second catheter 80 to establish the bridge stop regions.

Figure 19:
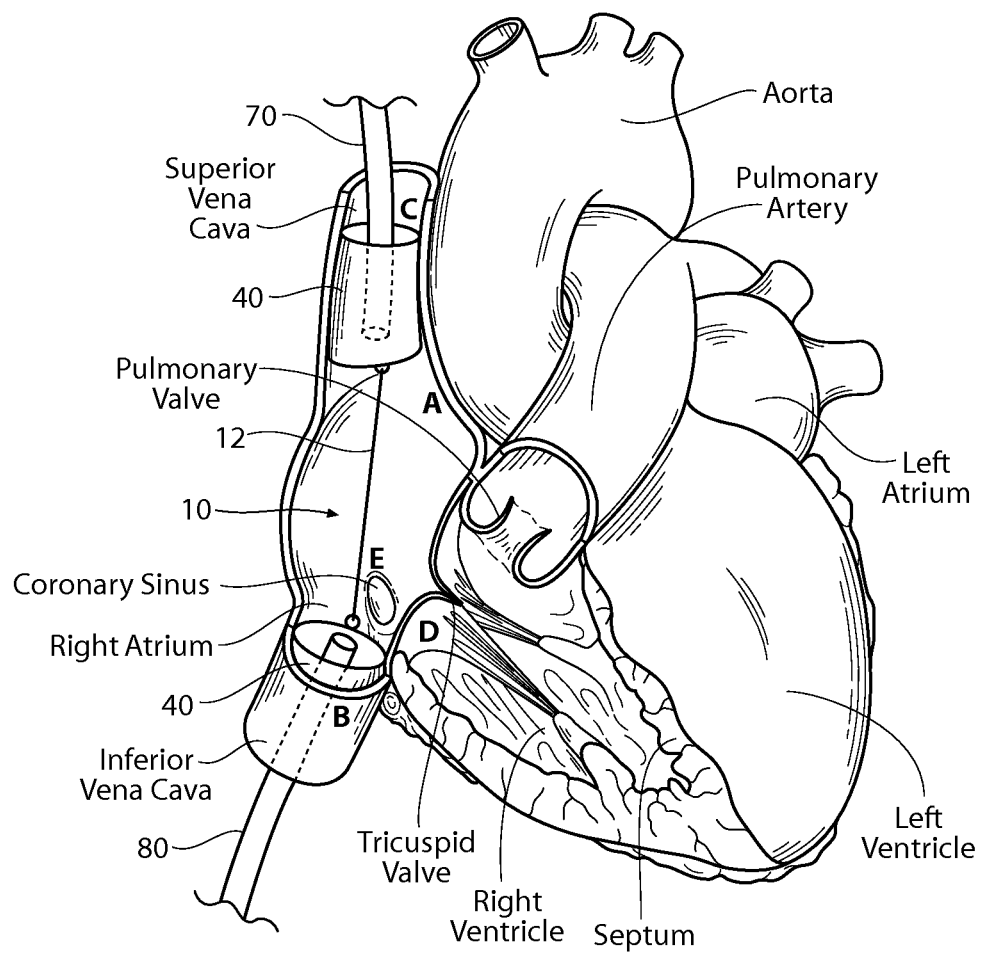
FIG. 19 is anatomic anterior perspective view of the right atrium and right ventricle, with portions broken away and in section to show the presence of representative catheter-based devices for implanting one or more systems of the types shown in FIGS. 11A to 11G, and showing previously deployed bridge stops and a bridging element extending between a bridge stop in the superior vena cava and a bridge stop in the inferior vena cava.

A first implantation step can be generally described as establishing the superior bridge stop region C and the inferior bridge stop region B. As can be seen in FIG. 19, the first catheter 70 is steered through the vasculature into the superior vena cava (or inferior vena cava). The second catheter 80 may also be steered through the vasculature and into the inferior vena cava (or superior vena cava). Once the first catheter 70 and the second catheter 80 are in their respective positions in the superior vena cava and the inferior vena cava, it is a function of the catheters 70, 80 to configure the bridge stop region C and B, i.e., deploy their respective bridge stops 40.

A second step can be generally described as establishing the bridging element 12. In one embodiment, the deployment catheter 80 may be used to deploy the superior vena cava bridge stop 40. Desirably, a pre-attached and predetermined length of bridging element 12 is coupled to the attachment point 42 of the bridge stop 40. The predetermined length of bridging element 12, e.g., two meters, extends from the superior bridge stop 40, through the right atrium, through the inferior vena cava, through the vasculature, and preferably remains accessible exterior the body. The predetermined length of bridging element 12 may be cut or detached in a future step, leaving implanted the portion extending from the superior bridge stop 40 to the inferior bridge stop 40.

With this configuration, the bridging element 12 must be passed through or around the attachment point 42 of the inferior vena cava bridge stop 40 before the bridge stop is deployed. This is simply achieved with the portion of the bridging element 12 extending exterior the body. The inferior vena cava bridge stop is now ready to be deployed. Alternatively, the inferior vena cava bridge stop may first be implanted, and then the bridging element 12 passed through or around its attachment point 42.

A third step can be generally described as adjusting the bridging element 12 for proper therapeutic effects. With the superior vena cava bridge stop region C, bridging element 12, and inferior vena cava bridge stop region B configured as previously described, a tension is placed on the bridging element 12. The implant 10 and associated regions may be allowed to settle for a predetermined amount of time, e.g., five or more seconds. The tricuspid valve and tricuspid valve regurgitation are observed for desired therapeutic effects. The tension on the bridging element 12 may be adjusted until a desired result is achieved. A bridge lock (not shown) is then allowed to secure the bridging element 12 to the attachment point 42 when the desired tension or measured length or degree of tricuspid regurgitation reduction is achieved.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:
1. A method of placing an implant within a heart chamber comprising:
deploying a guide wire in an intravascular path that extends from a first vascular access into the heart chamber and from the heart chamber to a second vascular access site different than the first vascular access site, the guide wire having a first end extending beyond the first vascular access site and a second end extending beyond the second vascular access site,
guiding a first catheter along the guide wire from the first vascular access site to a first bridge stop site within a wall of the heart chamber or adjacent vasculature;
deploying a first bridge stop at the first bridge stop site;
guiding a second catheter along the guide wire from the second vascular access site to a second bridge stop site within the wall of the heart chamber or adjacent vasculature;
deploying a second bridge stop at the second bridge stop site;
deploying a third bridge stop at a third bridge stop site within the wall of the heart chamber or adjacent vasculature with the first or second catheter;
coupling one end of a bridging element to the first bridge stop;
coupling another end of the bridging element to the second bridge stop; and
coupling the bridging element along an intermediate portion to the third bridge stop such that the bridging element spans across a single heart chamber, the single heart chamber comprising the respective heart chamber.

2. The method of claim 1 wherein the heart chamber comprises a right atrium.

3. The method of claim 1 further including placing the implant in tension within the heart chamber, thereby reshaping the heart chamber.

4. The method of claim 1 wherein the implant comprises a metallic material or polymer material or a metallic wire form structure or a polymer wire form structure or suture material or equine pericardium or porcine pericardium or bovine pericardium or preserved mammalian tissue.

5. The method of claim 1, wherein the first, second and third bridge stop sites comprise any of the vena cava, the coronary sinus and a tissue wall of an adjacent ventricle.

6. The method of claim 1, further comprising:
placing the bridging element in tension within the heart chamber so as to reshape a valve annulus of the heart chamber.

7. A method of placing an implant within a heart chamber comprising:
deploying a guide wire in an intravascular path that extends from a first vascular access into the heart chamber and from the heart chamber to a second vascular access site different than the first vascular access site, the guide wire having a first end extending beyond the first vascular access site and a second end extending beyond the second vascular access site;
deploying an exchange catheter in an intravascular path defined by the guide wire, the exchange catheter being deployed over the guide wire and having a first end extending beyond the first vascular access site and a second end extending beyond the second vascular access site;
coupling the implant to one end of the guide wire; and
pulling on the other end of the guide wire to pull the implant along at least a portion of the intravascular path through the exchange catheter and into the heart chamber, wherein pulling the implant into the heart chamber comprises pulling a bridging element of the implant across the heart chamber so that the bridging element extends from first and second bridge stops coupled to opposing end portions of the bridging element and to a third bridge stop coupled to an intermediate portion of the bridging element, wherein each of the first, second and third bridge stops are deployed within the wall of the heart chamber or adjacent vasculature such that the bridging element spans across a single heart chamber, the single heart chamber comprising the respective heart chamber.

8. The method of claim 7 wherein the heart chamber comprises a right atrium.

9. The method of claim 7, further comprising:
placing the implant in tension within the heart chamber thereby reshaping a valve annulus of the heart chamber so as to improve leaflet coaptation of the valve annulus.

10. The method of 9 wherein the bridging element comprises a metallic material or polymer material or a metallic wire form structure or a polymer wire form structure or suture material or equine pericardium or porcine pericardium or bovine pericardium or preserved mammalian tissue.

11. The method of claim 7, further comprising:
coupling the bridging element along one end to the first bridge stop at a first end of the bridging element;
coupling the bridging element along a second end opposite the first end to the second bridge stop; and
coupling the bridging element along an intermediate portion between the first and second end portions to the third bridge stop.

12. The method of claim 11, further comprising:
deploying each of the first and second bridge stops within the vasculature adjacent the heart chamber and deploying the third bridge stop within the wall of the heart chamber such that the bridging element spans across the heart chamber.

13. The method of claim 11, further comprising:
placing the bridging element in tension within the heart chamber so as to reshape a valve annulus of the heart chamber.

14. The method of claim 13, wherein the first, second, and third bridge stops comprise one or more bridge stops deployed within the vena cava or the coronary sinus.

15. The method of claim 13, wherein the first, second, and third bridge stops comprise one or more ventricle bridge stops deployed at least partly within the adjacent ventricle.

16. The method of claim 13, wherein the heart chamber is the right atrium and the valve annulus is of the tricuspid valve, the method further comprising:
deploying the first bridge stop within a superior vena cava of the heart;
deploying the second bridge stop within an inferior vena cava of the heart; and
deploying the third bridge stop within a ventricular tissue at or near the valve annulus.

17. The method of claim 13, wherein the heart chamber is the right atrium and the valve annulus is of the tricuspid valve, the method further comprising:
deploying the first bridge stop within a superior vena cava of the heart;
deploying the second bridge stop within a ventricular tissue at or near the valve annulus; and
deploying the third bridge stop within an inferior vena cava of the heart.

18. The method of claim 13, wherein the first, second, and third bridge stops comprise one or more bridge stops deployed within the vena cava or the coronary sinus.

19. The method of claim 13, wherein the first, second, and third bridge stops comprise one or more ventricle bridge stops deployed at least partly within the adjacent ventricle.

20. The method of claim 13, wherein the heart chamber is the right atrium and the valve annulus is of the tricuspid valve, the method further comprising:
deploying the first bridge stop within the superior vena cava;
deploying the second bridge stop within the inferior vena cava; and
deploying the third bridge stop, at least partly, within the right ventricle such that the bridging element crosses through or near a base of a leaflet of the tricuspid valve.

21. The method of claim 11, further comprising:
deploying each of the first and third bridge stops within the vasculature adjacent the heart chamber and deploying the second bridge stop within the wall of the heart chamber such that the bridging element spans across the heart chamber.

* * * * *